(12) United States Patent
St. John et al.

(10) Patent No.: US 7,351,430 B2
(45) Date of Patent: Apr. 1, 2008

(54) SHAPE-RETENTIVE HYDROGEL PARTICLE AGGREGATES AND THEIR USES

(75) Inventors: John V. St. John, Grapevine, TX (US); Daniel G. Moro, Dallas, TX (US); Bill C. Ponder, Grapevine, TX (US)

(73) Assignee: ULURU Inc., Addison, TX (US)

( * ) Notice: Subject to any disclaimer, the term of this patent is extended or adjusted under 35 U.S.C. 154(b) by 87 days.

(21) Appl. No.: 10/289,756

(22) Filed: Nov. 6, 2002

(65) Prior Publication Data

US 2004/0086548 A1    May 6, 2004

(51) Int. Cl.
 A61K 9/00   (2006.01)
 A61K 9/14   (2006.01)
 A61K 9/16   (2006.01)
 G02C 7/04   (2006.01)

(52) U.S. Cl. .............. 424/489; 424/400; 424/422; 424/427; 424/429; 424/501

(58) Field of Classification Search .......... 426/486; 424/488, 400, 489, 501, 422, 427, 429
See application file for complete search history.

(56) References Cited

U.S. PATENT DOCUMENTS

| | | | |
|---|---|---|---|
| 3,822,089 A * | 7/1974 | Wichterle | 351/160 R |
| 3,951,925 A * | 4/1976 | Mishima et al. | 526/73 |
| 3,963,685 A * | 6/1976 | Abrahams | 526/230.5 |
| 4,272,518 A | 6/1981 | Moro et al. | |
| 4,962,133 A | 10/1990 | Chromecek et al. | |
| 5,045,266 A | 9/1991 | Moro et al. | |
| 5,266,325 A | 11/1993 | Kuzma et al. | |
| 5,292,515 A | 3/1994 | Moro et al. | |
| 5,468,811 A * | 11/1995 | Moro et al. | 525/263 |
| 5,840,338 A * | 11/1998 | Roos et al. | 424/488 |
| 5,871,722 A * | 2/1999 | Nacht et al. | 424/78.03 |
| 5,945,457 A * | 8/1999 | Plate et al. | 514/772.1 |
| 6,068,859 A * | 5/2000 | Curatolo et al. | 424/490 |
| 6,306,177 B1 | 10/2001 | Felt et al. | |
| 6,521,431 B1 | 2/2003 | Kiser et al. | |
| 2003/0138490 A1 | 7/2003 | Hu et al. | |
| 2005/0118270 A1 | 6/2005 | Moro et al. | |

FOREIGN PATENT DOCUMENTS

GB    1 263 873    2/1972

OTHER PUBLICATIONS am Ende, et al., "Transport of ionizable drugs and proteins in crosslinked poly(acrylic acid) and poly(acrylic acid-*co*-2-hydroxyethyl methacrylate)," *Journal of Controlled Release* (1997), vol. 48, pp. 47-56.

(Continued)

*Primary Examiner*—Michael G. Hartley
*Assistant Examiner*—Simon J. Oh
(74) *Attorney, Agent, or Firm*—Foley & Lardner LLP

(57) ABSTRACT

The present invention is related to hydrogel particles and aggregates formed therefrom having characteristics including, without limitation, shape-retentiveness, elasticity, controllable pore sizes and controllable degradation rates that render them useful for a wide variety of applications including, without limitation, the controlled release of biologically active substances, in vivo medical devices, tissue growth scaffolding and tissue replacement.

19 Claims, 13 Drawing Sheets

Hydrogel Nanoparticles        Nanoparticle Aggregate

OTHER PUBLICATIONS

Ayhan, F. et al., "Optimization of urease immobilization onto non-porous HEMA incorporated poly(EGDMA) microbeads and estimation of kinetic parameters," *Bioresource Technology* (2002) vol. 81, pp. 131-140.

Beers, K. L. et al., "Atom Transfer Radical Polymerization of 2-Hydroxyethyl Methacrylate," *Macromolecules* (1999), vol. 32, pp. 5772-5776.

Bouillaguet, S. et al., "Effect of sub-lethal concentrations of HEMA (2-hydroxyethyl methacrylate) on THP-1 human monocyte-macrophages, in vitro," *Dental Materials* (2000), vol. 16, pp. 213-217.

Brahim, S. et al., "Kinetics of glucose oxidase immobilized in p(HEMA)-hydrogel microspheres in a packed-bed bioreactor," *Journal of Molecular Catalysis B: Enzymatic* (2002), vol. 18, pp. 69-80.

Brier-Russell, D. et al., "In Vitro Assessment of Interaction of Blood with Model Surfaces: Acrylates and Methacrylates," *journal of Colloid and Interface Science* (1981), vol. 81, pp. 311-318.

Dalton, P. D. et al., "Manufacture of poly(2-hydroxyethyl methacrylate-co-methyl methacrylate) hydrogel tubes for use as nerve guidance channels," *Biiomaterials* (2002), vol. 23, pp. 3843-3851.

Debord, J.D. et al., "Thermoresponsive Photonic Crystals," *The Journal of Physical Chemistry* (2000), vol. 104, No. 27, pp. 6327-6331.

Denizli, A. et al., "Monosize and non-porous p(HEMA-co-MMA) microparticles designed as dye- and metal-chelate affinity sorbents," *Colloids and Surfaces A: Physicochemical and Engineering Aspects* (2000), vol. 174, pp. 307-317.

Dziubla, T. D. et al., "Evaluation of porous networks of poly(2-hydroxyethyl methacrylate) as interfacial drug delivery devices," *Biomaterials* (2001), pp. 2893-2899.

Frutos, P. et al., "Release of gentamicin sulphate from a modified commercial bone cement. Effect of (2-hyroxyethyl methacrylate) comonomer and poly(N-vinyl-2-pyrrolidone) additive on release mechanism and kinetics," *Biomaterials* (2002), vol. 23, pp. 3787-3797.

Gallardo, A. et al., "Controlled release of cyclosporine from VP-MEMA copolymer systems of adjustable resorption monitorized by MEKC," *Biomaterials* (2000), vol. 21, pp. 915-921.

Gallardo, A. et al., "Modulated release of cyclosporine from soluble vinyl pyrrolidone-hydroxyethyl methacrylate copolymer hydrogels A correlation of 'in vitro' and 'in vivo' experiments," *Journal of Controlled Release* (2001), vol. 72, pp. 1-11.

Garrett, Q. et al., "Effect of charged groups on the adsorption and penetration of proteins onto and into carboxymethylated poly(HEMA) hydrogels," *Biomaterials* (1998), vol. 19, pp. 2175-2186.

Graham, N. B. et al., "Nanogels and microgels: The new polymeric materials playground," *Pure & Appl. Chem.* (1998), vol. 70, No. 6, pp. 1271-1275.

Hacioglu, B. et al., "Polymerization kinetics of HEMA/DEGDMA: using changes in initiation and chain transfer rates to explore the effects of chain-length-dependent termination," *Biomaterials* (2002), vol. 23, pp. 4057-4064.

Horak, D. et al., "Hydrogels in endovascular embolization," *Biomaterials* (1997), vol. 18, pp. 1355-1359.

Hsiue, G. et al., "Poly(2-hydroxyethyl methacrylate) film as a drug delivery system for pilocarpine," *Biomaterials* (2001), vol. 22, pp. 1763-1769.

Hu, Z. et al., "Polymer Gel Nanoparticle Networks," *Advanced Materials* (2000), vol. 12, No. 16, pp. 1173-1176.

Hutcheon, G.A. et al., "Water absorption and surface properties of novel poly(ethylmethacrylate) polymer systems for use in bone and cartilage repair," *Biomaterials* (2001), vol. 22, pp. 667-676.

Klisch, J. et al., "Combined stent implantation and embolization with liquid 2-polyhydroxyethyl methacrylate for treatment of experimental canine wide-necked aneurysms," *Interventional Neuroradiology* (2002), vol. 44, pp. 503-512.

Lesny, P. et al., "Polymer hydrogels usable for nervous tissue repair," *Journal of Chemical Neuroanatomy* (2002), vol. 23, pp. 243-247.

Liu, Q. et al., "Preparation of macroporous poly(2-Hydroxyethyl methacrylate) hydrogels by enhanced phase separation," *Biomaterials* (2000), vol. 21, pp. 2163-2169.

Lyon, L. A. et al., "Responsive Microgel Photonic Crystals," *Polymer Preprints* (2002), vol. 43, pp. 24-25.

Lyon, L. A. et al., "Tunable Kinetics of Core-Shell Microgel Volume Phase Transitions," *Polymer Preprints* (2002), vol. 43, pp. 363-364.

Noda, M. et al., "Sublethal, 2-week exposures of dental material components alter TNF-60 secretion of THP-1 monocytes," *Dental Materials* (2003), pp. 1-5.

Nojiri, C. et al., "Nonthrombogenic Polymer Vascular Prosthesis," *Artificial Organs* (1995), vol. 19, No. 1, pp. 32-38.

Pashley, D. H. et al., "Permeability of demineralized dentin to HEMA," *Dental Materials* (2000), vol. 16, pp. 7-14.

Ramakrishna, S. et al., "Biomedical applications of polymer-composite materials: a review," *Composites Science and Technology* (2001), vol. 61, pp. 1189-1224.

Reichl, F. X., "Biological clearance of HEMA in guinea pigs," *Biomaterials* (2002), vol. 23, pp. 2135-2141.

Robinson, K. L., "Controlled Polymerization of 2-Hydroxyethyl Methacrylate by ATRP at Ambient Temperature," *Macromolecules* (2001), vol. 34, pp. 3155-3158.

Rogach, A. L. et al., "Electrophoretic Deposition of Latex-Based 3D Colloidal Photonic Crystals: A Technique for Rapid Production of High-Quality Opals," *Chem Mater.* (2000), vol. 12, pp. 2721-2726.

Sefc, L. et al., "Development of hydrogel implants for urinary incontinence treatment," *Biomaterials* (2002), vol. 23, pp. 3711-3715.

Sefton, M. V. et al., "Making microencapsulation work: conformal coating, immobilization gels and in vivo performance," *Journal of Controlled Release* (2000), vol. 65, pp. 173-186.

Seidel, J. M. et al., "Synthesis of PolyHEMA Hydrogels for Using as Biomaterials," *Materials Research* (2000), vol. 3, No. 3, pp. 79-83.

Tanaka, M. et al., "Study on kinetics of early stage protein adsorption on poly(2-methyoxyethylacrylate) (PMEA) surface," *Colloids and Surfaces A: Physicochemical and Engineering Aspects/* (2002), vol. 203, pp. 195-204.

Tanaka, M. et al., "Blood compatible aspects of poly(2-methoxyethylacrylate) (PMEA)—relationship between protein adosrption and platelet adhesion on PMEA surface," *Biomaterials* (2000), vol. 21, pp. 1471-1481.

Yoshi, E., "Cytotoxic effects of acrylates and methacrylates: Relationships of monomer structures and cytotoxicity," *J. Biomed Mater. Res.* (1997), vol. 37, pp. 517-524.

Klein et al. (2003), "Preparation of Monodisperse PMMA Microspheres in Nonpolar Solvents by Dispersion Polymerization with a Macromonomeric Stabilizer," *Colloid Polym. Sci.* 282:7-13.

*Radiation Synthesis and Modification of Polymers for Biomedical Applications* (2002), pp. 1-3, International Atomic Energy Agency, Austria.

Szkurhan & Georges (2004), "Stable Free-Radical Emulsion Polymerization," *Macromolecules* 37:4776-4782.

* cited by examiner

SHAPE-RETENTIVE HYDROGEL PARTICLE AGGREGATES AND THEIR USES

FIELD OF THE INVENTION

This invention relates to the fields of organic chemistry, polymer chemistry, pharmaceutical chemistry and material science. In particular, it relates to shape-retentive aggregates of hydrogel particles and their uses.

BACKGROUND OF THE INVENTION

The discussion that follows is provided as background information to aid the reader in understanding the present invention and is not intended, nor is it to be construed, as being prior art to the invention.

A gel is a three-dimensional polymeric network that has absorbed a liquid to form a stable, usually soft and pliable, composition having a non-zero shear modulus. The liquid contributes a substantial percent of the overall volume of the composition. When the liquid is water, the gel is called a hydrogel. Due to their unique composition, i.e., largely water absorbed into a biologically inert polymeric matrix, hydrogels have found use in numerous biomedical applications.

For example, hydrogels are the virtual foundation of the soft contact lens industry. They are also used as wound dressings, both with and without incorporated medicaments that can be released from the matrix to aid in the healing process (U.S. Pat. Nos. 3,963,685 and 4,272,518). Hydrogels have been used as artificial sphincters for treatment of urinary incontinence by virtue of their ability to swell upon absorption of water (Sefc, et al., *Biomaterials*, 2002, 23:3711). They have also been used a coatings to enhance the wettability of medical devices such as blood filters (U.S. Pat. No. 5,582,794). In addition, hydrogels have found substantial use as vehicles for the sustained release of biologically active substances.

Thus, European Pat. App. No. 0246653 describes a drug delivery device that includes a partially hydrated, non-biodegradable hydrogel as a release-rate-limiting barrier. U.S. Pat. No. 5,292,515 discloses a method of preparing a hydrophilic reservoir drug delivery device using a variety of hydrogel compositions. Davidson, et al. report the use of hydrogel membranes for the controlled delivery of luteinizing hormone-releasing hormone (*Proceed. Inter. Symp. Cont. Rel. Bioact. Materials*, 1988, 15).

In all the above instances, the hydrogel used is in bulk polymeric form, that is, an amorphous mass of material with no discernable regular internal structure. The amorphous nature of the hydrogel may affect the homogeneity of a composite of the gel with other substances. Furthermore, bulk hydrogels usually have slow swelling rates due to the large internal volume compared to the surface area through which water can be absorbed. Their size makes them relatively poor vehicles for controlled release of bioactive substances. That is, a substance dissolved or suspended in the absorbed water will diffuse out of the hydrogel at markedly different rates depending on where it is in the matrix. A substance at or near the surface of the hydrogel will easily escape the gel matrix but material deeper within the matrix will have to diffuse a much longer distance before reaching the outer surface of the gel and being released. This situation can be ameliorated to some extent by the use of particulate hydrogels. If the particles are sufficiently small, substances dispersed in them will diffuse to the surface and be released at essentially the same rate.

Particulate hydrogels can be formed ab initio, for example, without limitation, by direct or inverse emulsion polymerization (Landfester, et al., *Macromolecules*, 2000, 33:2370) or they can be created from bulk hydrogels by drying the hydrogel, grinding the resulting xerogel and sieving the ground material to obtain particles of a desired size. The particles can then be re-hydrated to form particulate hydrogels. Using either of these approaches, particles having micro ($10^{-6}$ meters (m)) to nano ($10^{-9}$ m) range diameters can be produced. As noted above, with their small volumes, any given molecule of a bioactive substance entrapped within a particle has almost the same distance to travel to reach the outer surface of the particle as any other molecule, giving rise to the possibility of zero order, or very nearly so, release kinetics. Using particulate hydrogels, however, also has its problems. Among these are controlling the dissemination of the particles to, and localization of them at, a particular target site. In addition, as mentioned previously, bulk hydrogels can be shape-retentive rendering them useful in such applications as artificial sphincters, tissue delivery vehicles, tissue replacement (artificial cartilage) materials, etc., while currently available particulate hydrogel aggregates, cannot.

What is needed is a material that has the desirable characteristics of bulk hydrogels, shape-retention and, in certain applications, elastomericity, and of particulate hydrogel aggregates, individually small volumes that offer more controllable substance delivery rates. The present invention provides such a material—a shape-retentive, aggregate of hydrogel particles. It also provides uses for the aggregates including, but not limited to, the controlled delivery of bioactive substances.

SUMMARY OF THE INVENTION

Thus, an aspect of this invention is a shape-retentive aggregate comprising a plurality of hydrogel particles, each particle comprising a plurality of polymeric strands obtained by polymerization of one or more monomers at least one of which comprises one or more hydroxy and/or one or more ether groups; from 10 to 90 weight percent of one or more absorbed liquid(s), at least one of which comprises one or more hydroxy groups, wherein the liquid(s) is/are absorbed into the hydrogel particles; and, from 10 to 90 weight percent of one or more non-absorbed liquids, which may be the same as, or different from, the absorbed liquid(s) and at least one of which comprises one or more hydroxy groups, the non-absorbed liquid occupying voids between the hydrogel particles of the aggregate.

Another aspect of this invention is a shape-retentive aggregate comprising at least 50 volume percent of hydrogel particles, each hydrogel particle comprising a plurality of polymeric strands obtained by polymerization of one or more monomers at least one of which comprises one or more hydroxy and/or one or more ether groups; up to 50 volume percent of one or more working substances; from 10 to 90 weight percent of one or more absorbed liquid(s), at least one of which comprises one or more hydroxy groups, wherein the liquid(s) is(are) absorbed into the hydrogel particles; and, from 10 to 90 weight percent of one or more non-absorbed liquids, which may be the same as, or different from, the absorbed liquid(s) and at least one of which comprises one or more hydroxy groups, the non-absorbed liquid occupying voids between the hydrogel particles of the aggregate, wherein the working substance(s) is(are) dissolved or suspended in the absorbed liquid or the working substance(s) is(are) dissolved or suspended in the non-absorbed liquid or one or more of the working substance(s) is(are) dissolved or suspended in the absorbed liquid and one or more of the working substances is(are) dissolved or suspended in the non-absorbed liquid.

In an aspect of this invention, the working substance comprises one or metals, or alloys thereof.

In an aspect of this invention, the working substance comprises one or more metals individually having oxidation states of one or higher.

In an aspect of this invention, the working substance comprises one or more semiconductor elements or compounds.

In an aspect of this invention, the working substance comprises one or more pharmaceutical agents.

In an aspect of this invention, the working substance further comprises one or more pharmaceutically acceptable excipients.

In an aspect of this invention, the pharmaceutical agent is a peptide or protein.

In an aspect of this invention, the one or more pharmaceutical agents are useful for the treatment of cancer.

In an aspect of this invention, the one or more pharmaceutical agents are useful for the treatment of coronary artery disease.

In an aspect of this invention, the one or more pharmaceutical agents are useful for the treatment of respiratory diseases.

In an aspect of this invention, the one or more pharmaceutical agents are useful for the treatment of infectious diseases.

A further aspect of this invention is a method for preparing a composition for controlled release of a working substance comprising adding one or more monomers, at least one of which includes one or more hydroxy and/or one or more ether groups, to one or more liquids, at least one of which includes one or more hydroxy groups; adding from 0.01 to 10 mol percent of a surfactant to the liquid(s); polymerizing the monomers to form a suspension in the liquid of hydrogel particles comprising a plurality of polymeric strands and from 10 to 90% of an absorbed liquid(s); dissolving or suspending one or more working substance(s) in remaining non-absorbed liquid(s); and, removing non-absorbed liquids until a shape-retentive aggregate forms.

In the above method, the working substance(s) is(are) dissolved or suspended in the remaining non-absorbed liquid(s) after polymerization of the monomers resulting in a shape-retentive aggregate comprising 10 to 90 weight percent working-substance-containing, non-absorbed liquid and hydrogel particles comprising 10 to 90 weight percent non-working-substance-containing absorbed liquid, in an aspect of this invention.

In the above method, the working substance(s) is(are) dissolved or suspended in the liquid(s) before polymerization of the monomers resulting in a shape-retentive aggregate comprising 10 to 90 weight percent working-substance-containing, non-absorbed liquid and hydrogel particles comprising 10 to 90 weight percent working-substance-containing absorbed liquid, in another aspect of this invention.

In the above method, after polymerization but before removing non-absorbed liquid to form the shape-retentive aggregate, the working substance is removed from the non-absorbed liquid resulting in a shape-retentive aggregate comprising 10 to 90 weight percent non-working-substance-containing, non-absorbed liquid and hydrogel particles comprising 10 to 90 weight percent working-substance-containing absorbed liquid, in an aspect of this invention.

In an aspect of this invention, the shape-retentive aggregate is elastomeric.

In an aspect of this invention, the monomer(s) is/are selected from the group consisting of a 2-alkenoic acid, a hydroxy(2C-4C)alkyl 2-alkenoate, a hydroxy(2C-4C)alkoxy(2C-4C)alkyl 2-alkenoate, a (1C-4C)alkoxy(2C-4C)alkoxy(2C-4C)alkyl 2-alkenoate and a vicinyl epoxy(1C-4C)alkyl 2-alkenoate.

In an aspect of this invention, the monomer(s) is(are) selected from the group consisting of acrylic acid, methacrylic acid, 2-hydroxyethyl acrylate, 2-hydroxyethylmethacrylate, diethyleneglycol monoacrylate, diethyleneglycol monomethacrylate, 2-hydroxypropyl acrylate, 2-hydroxypropyl methyacrylate, 3-hydroxypropyl acrylate, 3-hydroxypropyl methacrylate, dipropylene glycol monoacrylate, dipropylene glycol monomethacrylate, gylcidyl methacrylate, 2,3-dihydroxypropyl methacrylate, glycidyl acrylate and glycidyl methacrylate.

In an aspect of this invention the monomer is 2-hydroxyethyl methacrylate, 3-hydroxypropyl methacrylate, or a combination thereof.

In an aspect of this invention the absorbed and the non-absorbed liquids are independently selected from the group consisting of water, a (1C-10C) alcohol, a (2C-8C) polyol, a (1C-4C)alkyl ether of a (2C-8C)polyol, a (1C-4C) acid ester of a (2C-8C)polyol; a hydroxy-terminated polyethylene oxide, a polyalkylene glycol and a hydroxy(2C-4C)alkyl ester of a mono, di- or tricarboxylic acid.

In an aspect of this invention, the absorbed and the non-absorbed liquids are independently selected from the group consisting of water, methanol, ethanol, isopropyl alcohol, ethylene glycol, diethylene glycol, triethylene glycol, polyethylene glycol 200-600, propylene glycol, dipropylene glycol, 1,4-butanediol, 2,3-butanediol, 1,6-hexanediol, 2,5-hexanediol, ethylene glycol monomethyl ether, ethylene glycol monoethyl ether, methylcellosolve ether, ethylene glycol monoacetate, propylene glycol monomethyl ether, glycerine, glycerol monoacetate, tri(2-hydroxyethyl) citrate, di(hydroxypropyl)oxalate, glycerine, glyceryl monoacetate, glyceryl diacetate, glyceryl monobutyrate and sorbitol.

In an aspect of this invention, the absorbed liquid is water.

In an aspect of this invention, the non-absorbed liquid is water.

In an aspect of this invention, the absorbed and the non-absorbed liquid are water.

In an aspect of this invention, the hydrogel particles comprise from 0.1 to 15% mol percent of a cross-linking agent.

In an aspect of this invention, the cross-linking agent is selected from the group consisting of ethylene glycol diacrylate, ethylene glycol dimethacrylate, 1,4-dihydroxybutane dimethacrylate, diethylene glycol dimethacrylate, propylene glycol dimethacrylate, diethylene glycol dimethacrylate, dipropylene glycol dimethacrylate, diethylene glycol diacrylate, dipropylene glycol diacrylate, divinyl benzene, divinyltoluene, diallyl tartrate, diallyl malate, divinyl tartrate, triallyl melamine, N,N'-methylene bisacrylamide, diallyl maleate, divinyl ether, 1,3-diallyl 2-(2-hydroxyethyl) citrate, vinyl allyl citrate, allyl vinyl maleate, diallyl itaconate, di(2-hydroxyethyl) itaconate, divinyl sulfone, hexahydro-1,3,5-triallyltriazine, triallyl phosphite, diallyl benzenephosphonate, triallyl aconitate, divinyl citraconate, trimethylolpropane trimethacrylate and diallyl fumarate.

In an aspect of this invention, the cross-linking agent is selected from the group consisting of α-hydroxy acid esters.

In an aspect of this invention, the plurality of hydrogel particles is of narrow polydispersivity.

In an aspect of this invention, the hydrogel particles are uncharged, charged or a combination thereof.

In an aspect of this invention, the plurality of hydrogel particles comprises particles of two or more different sizes and/or two or more different chemical compositions.

In an aspect of this invention, the cross-linked polymer strands have an average molecular weight of from about 25,000 to about 2,000,000.

In an aspect of this invention, the aggregate is degradable.

In an aspect of this invention, the hydrogel particles of the aggregate are degradable.

DETAILED DESCRIPTION OF THE INVENTION

Brief description of the tables

Table 1 is a comparison of the size of poly (2-hydroxyethyl methacrylate) (HEMA)-co-methacrylic acid (MAA)) hydrogel particle as a function of MM content and polymerization pH.

Table 2 is a comparison of the size of poly (HEMA-co-(monomer)) hydrogel particles as a function of the content of various monomers and of polymerization pH.

Table 3 shows the weight percent of a variety of substances that were incorporated into ethyleneglycol dimethacrylate cross-linked poly(HEMA-co-MM) hydrogel particles.

Table 4 shows a comparison of the resilience and springiness of an aggregate formed from polyHEMA hydrogel particles, an aggregate formed from poly (HEMA-co-10% MM) and a polyHEMA bulk hydrogel.

Table 5 shows the resilience and springiness of the materials in Table 4 after 10 minutes of relaxation.

Table 6 shows the weight percent of a variety of substances that were entrapped in the voids between poly (HEMA-co-MM) hydrogel particles of an aggregate of this invention.

DEFINITIONS

Figure 1:
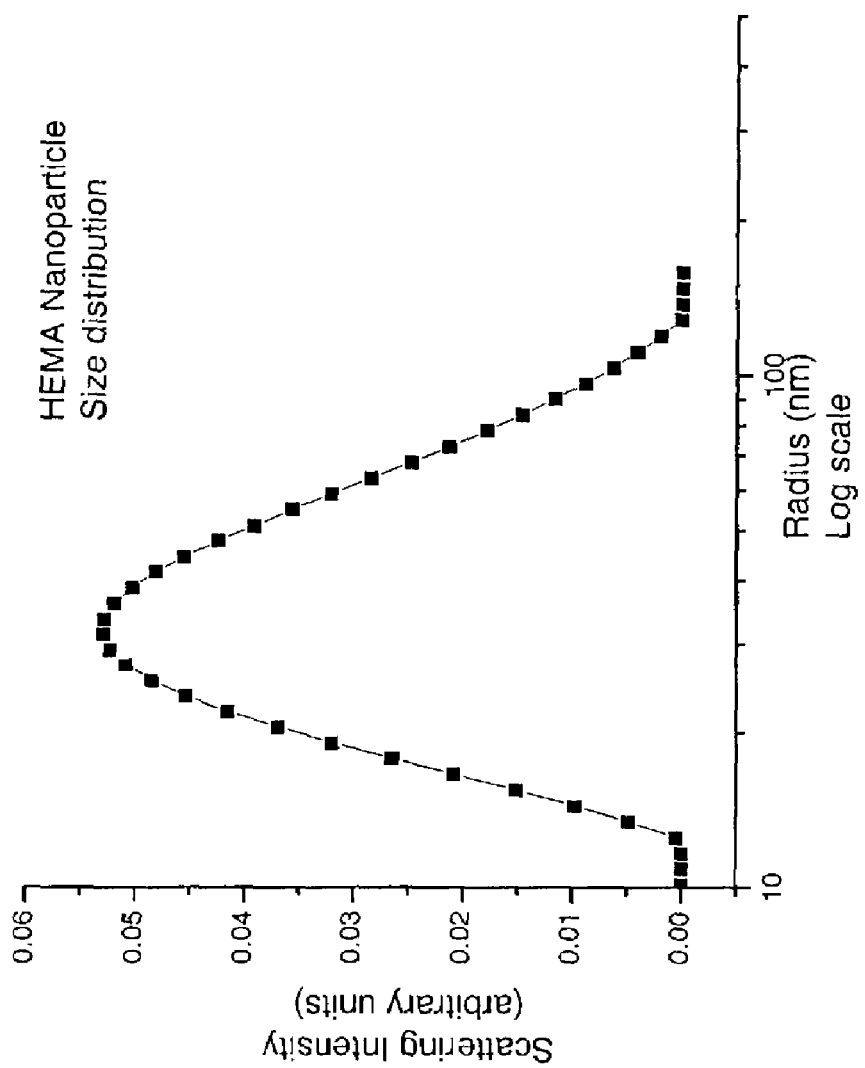
FIG. 1 is a graph of the size distribution of polyHEMA hydrogel particles formed by the polymerization method of this invention.

As used herein, the term "hydrogel" refers to a three-dimensional polymeric structure that itself is insoluble in water but which is capable of absorbing and retaining large quantities of water to form a stable, often soft and pliable, structure.

As used herein, a "hydrogel particle" refers to a microscopic or submicroscopic quantity of a hydrogel in a discrete shape, usually, but not necessarily, spherical or substantially so.

As used herein, the term "aggregate" refers to a bulk material composed of a plurality of hydrogel particles held together by inter-particle and particle-liquid forces such as, without limitation, hydrogen bonds.

As used herein, the term "shape-retentive" refers to a hydrogel aggregate that when cut, molded or otherwise conformed to a particular three-dimensional shape, maintains that shape indefinitely when in the hydrated state.

As used herein, the term "elastomeric" refers to hydrogel aggregate that can be stretched to at least 200% its original length and when the stress is removed, immediately returns to its approximate original length.

As used herein, the term "monomer" refers to a small chemical entity which is capable of reacting with itself to form a macromolecule of repeating units. The macromolecule is called a polymer. Two or more monomers may react to form a polymer in which each of the monomers is repeated numerous times. These latter polymers are referred to as copolymers to reflect the fact that they contain more than one monomer.

As used herein, the term "polydispersity" refers to the range of diameters of the hydrogel particles obtained using the methods of this invention. "Narrow polydispersity" refers to a plurality of hydrogel particles that have a range of diameters with deviations less than 10% from the average diameter.

As used herein, the phrase "two or more different sizes" refers to two or more pluralities of hydrogel particles, the particles of each plurality having an average diameter different from each of the other pluralities.

As used herein, "two or more different chemical compositions" refers to two or more pluralities of hydrogel particles, wherein the particles of each plurality are formed from different monomers, different ratios of monomers if two or more monomers are used and/or different cross-linking agents.

As used herein, the term "degradable" refers to a characteristic of some of the aggregates and hydrogel particles of this invention, the characteristic being loss of structural stability under selected chemical and/or physical conditions such as, without limitation, temperature, abrasion, pH, ionic strength, electrical voltage and/or current, acidity, basicity, solvent effects and the like.

As used herein, the term "dissolved" refers to a substance that forms a solution with a liquid of this invention. A solution refers to a mixture wherein the components form a single phase in which they are uniformly and stably distributed.

As used herein, the term "suspended" refers to a substance that is insoluble in a liquid of this invention but that forms a second phase consisting of discrete particles of the substance distributed relatively uniformly, but unstably, in the liquid. By unstably is meant that the phases will separate with time, if left to stand, or under the influence of external forces such as centrifugation, filtration and the like.

As used herein, a "working substance" refers to any substance that is placed in a hydrogel particle or an aggregate of this invention for the purpose of achieving a particular purpose, goal, operation or process appropriate for that substance. Examples of working substances, without limitation, include pharmaceutical agents, agrichemical agents, radiopaque substances, radioactive substances, pigments, dyes, metals, semiconductors, dopants, chemical intermediates, acids, bases and biological materials such as genes, proteins, antibodies, antigens, polypeptides, DNA, RNA and ribozymes.

As used herein, a "metal" refers to those elements in the periodic table of the elements that are distinguished by their luster, malleability, conductivity and ability to form positive ions. In particular, a metal for the purposes of this invention, refers to the transition elements, Groups IB, IIB, IIIB (including the rare earth and actinide metals), IVB, VB, VIB, VIIB and VIII of the period table.

As used herein, the term "noble metal" refers to gold, silver, platinum, palladium, ruthenium, rhodium and iridium.

As used herein, an "alloy" refers to a substance possessing metallic properties and composed of two or more elements at least one of which must be a metal. Examples of alloys include, but are not limited to, bronze, brass and stainless steel.

As used herein, the term "oxidation state" refers to the charge on a metallic ion, which charge is the result of the loss of electrons by an atom of the element. Thus, the "zero oxidation state" or "ground state" is the metal itself with its full complement of electrons. An "oxidation state of one" connotes a single positive charge equal to the charge of a proton and results from the loss of one electron, an "oxidation state of two" connotes a positive charge equal to that of two protons and results from the loss of two electrons, and so on.

As used herein, a "semiconductor element or compound" refers to a crystalline material having electrical resistivity values intermediate between those of insulators and those of metals (conductors); i.e., about $10^{-2}$ to $10^9$ ohm-cm. Semiconductors will conduct electricity under some conditions but not others. Perhaps the best known semiconductor element is silicon. Other examples of elemental semiconductors include, but are not limited to, antimony, arsenic, boron, carbon, gemanium, selenium, sulfur and tellurium. Examples, without limitation, of semiconductor compounds include gallium arsenide, indium antimonide and the oxides of most metals.

A "hydroxy" group refers to an —OH group.

An "ether" group refers to an R—O—R' group in which R and R' are independently alkyl, cycloalkyl, aryl, heteroaryl or heteroalicyclic carbon atoms.

As used herein, the term "alkyl" refers to a straight or branched chain saturated aliphatic hydrocarbon. Preferably, the alkyl group consists of 1 to 20 carbon atoms (whenever a numerical range such as, for example, "1-8" or "1 to 8" is provided herein, it means that the group may consist of 1 carbon atom, 2 carbon atoms, 3 carbon atoms, etc., up to and including 8 carbon atoms). More preferably, an alkyl group of this invention is a medium size alkyl having 1 to 10 carbon atoms. Most preferably, it is a lower alkyl having 1 to 4 carbon atoms. The size of an alkyl may be indicated by the formula (aC-bC) alkyl where a and b are integers from 1 to 20 and indicate how may carbons are in the alkyl chain. For example, a (1C-4C) alkyl refers to a straight or branched chain alkyl consisting of 1, 2, 3 or 4 carbon atoms. An alkyl group may be substituted or unsubstituted.

A "cycloalkyl" group refers to a 3 to 8 member all-carbon monocyclic ring. The designation (3C-6C)cycloalkyl, for example, refers to a 3-, 4-, 5- or 6-member all-carbon ring. A cycloalkyl group may contain one or more double bonds but it does not contain a fully conjugated pi-electron system; i.e., it is not aromatic. Examples, without limitation, of cycloalkyl groups are cyclopropane, cyclobutane, cyclopentane, cyclopentene, cyclohexane, cyclohexadiene, adamantane, cycloheptane and, cycloheptatriene. A cycloalkyl group may be substituted or unsubstituted.

An "alkenyl" group refers to an alkyl group, as defined herein, having at least two carbon atoms and at least one carbon-carbon double bond. As used herein, (2C-4C)alkenyl, for example, refers to a 2, 3, or 4 carbon alkenyl group. An alkenyl group may be substituted or unsubstituted.

An "aryl" group refers to an all-carbon monocyclic or a fused-ring polycyclic (i.e., rings which share adjacent pairs of carbon atoms) group having a completely conjugated pi-electron system. Examples, without limitation, of aryl groups are phenyl, naphthalenyl and anthracenyl. The aryl group may be substituted or unsubstituted.

A "heteroaryl" group refers to a monocyclic or fused ring in which one or more of the rings contains one or more atoms selected from the group consisting of nitrogen, oxygen and sulfur and, in addition, sufficient double bonds to establish a fully conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine and carbazole. A heteroaryl group may be substituted or unsubstituted.

A "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. The heteroalicyclic ring may be substituted or unsubstituted.

When it is stated that a chemical group can be "substituted or unsubstituted," it is understood that such substitution involves chemical groups that are well-known to those skilled in the art and that can be covalently bonded to the group being substituted without undue experimentation to make and use in the invention herein. Such groups include, without limitation, F, Cl, BR, I, —CN, —NO$_2$, —OH, —COOH, —CHO, —NRR' and —OR, wherein R and R' are independently alkyl, cycloalkyl, aryl, heteroaryl or heteroalicyclic.

As used herein the term "absorbed" refers to a liquid that is taken into and stably retained in the interior, that is, internal to the outer surface, of a hydrogel particle of this invention.

As used herein, "non-absorbed" refers to a liquid that is external to the outer surface of a hydrogel particle of this invention. When the non-absorbed liquid is contained in an aggregate of this invention, it occupies voids between the hydrogel particles that comprise the aggregate.

Figure 6:
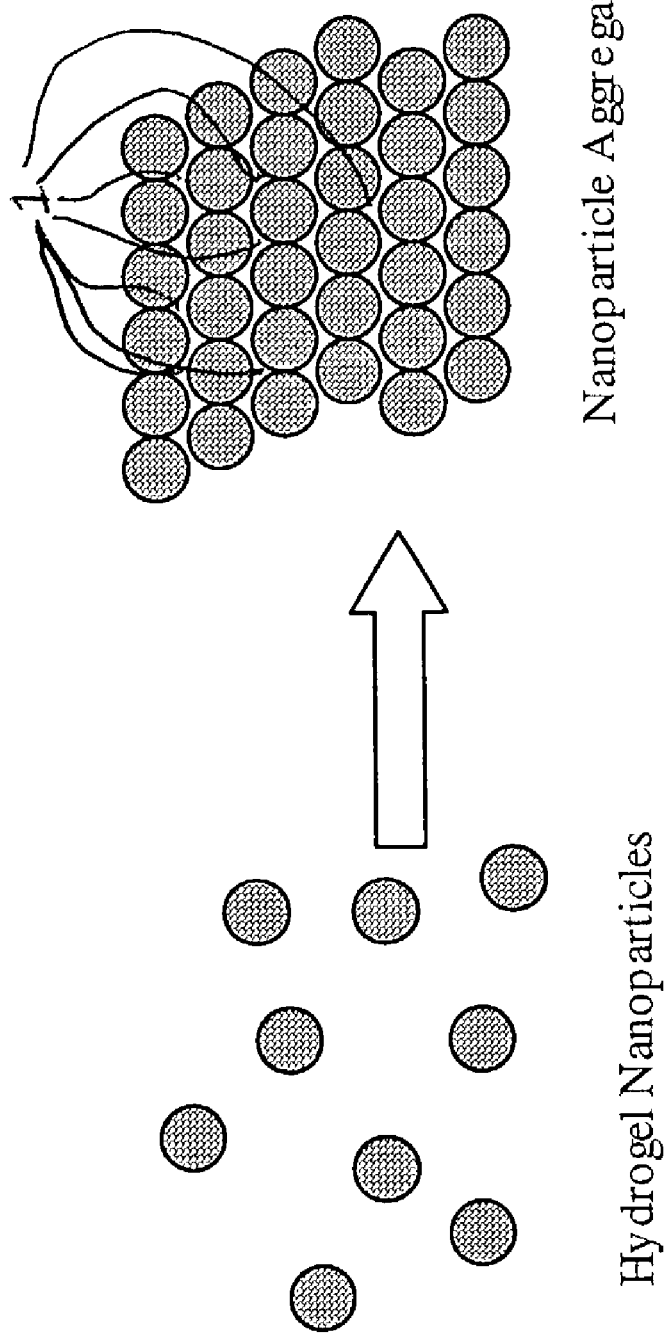
FIG. 6 is a schematic representation of the formation of an aggregate of this invention by centrifugation of a suspension of narrow dispersivity hydrogel particles.

As used herein, the phrase "voids between the hydrogel particles" refers to the regions 1 in FIG. 6. The hydrogel particles, which are essentially spherical, touch along their circumferences and leave a certain amount of open space between them that they cannot fill and still maintain their spherical shape. When the particles are spherical and are close-packed, the volume of the voids can be calculated as 0.414 times the average radius of the spheres.

As used herein, a "cross-linking agent" refers to a di, tri, or tetrafunctional chemical entity that forms covalent bonds with other functional groups attached to monomers that have been incorporated into two or more different polymeric strands or are located at two or more different locations in the same strand resulting in a branched three-dimensional structure.

A "hydrogen bond" refers to the electronic attraction between a hydrogen atom covalently bonded to a highly electronegative atom and another electronegative atom having at least one lone pair of electrons. The strength of a hydrogen bond, at about 23 kJ (kilojoules) mol$^{-1}$, is between that of a covalent bond, about 500 kJ mol$^{-1}$, and a van der Waals attraction, about 1.3 kJ mol$^{-1}$. Hydrogen bonds have a marked effect on the physical characteristics of a compound capable of forming them with among molecules of itself. For example, ethanol has a hydrogen atom covalently bonded to an oxygen atom, which also has a pair of unshared (i.e., a "lone pair") electrons and, therefore, ethanol is capable of hydrogen bonding. Ethanol has a boiling point of 78° C. In general, compounds of similar molecular weight are expected to have similar boiling points. However, dimethyl ether, which has exactly the same molecular weight as ethanol but which is not capable of hydrogen bonding between molecules of itself, has a boiling point of −24° C., almost 100 degrees lower than ethanol. Hydrogen bonding between the ethanol molecules has made ethanol act as if it were substantially higher in molecular weight.

As used herein, a "charged" hydrogel particle refers to a particle that has a localized positive or negative charge due to ionic content of the monomers making up the polymer strand of the particle and the environment in which these particles find themselves. For example, without limitation, hydrogel particles comprising acrylic acid as a co-monomer will, under basic conditions, exist in a state in which some or all of the acid groups are ionized, i.e., the —COOH groups become —COO$^-$ groups in which one of the oxygen atoms carries a negative charge. Another example is the amino (—NH$_2$) group, which, in an acidic environment, will form an ammonium (—NH$_3^+$) ion.

As used herein, a "biologically active substance" refers to any chemical substance that has a pharmacological effect on a living organism. This includes "pharmaceutical agents," which, as used herein, relate to small molecule pharmaceuticals such as, without limitation, antibiotics, chemotherapeutics (in particular the platinum compounds and taxol and its derivatives), analgesics, antidepressants, antiallergenics, antiarryhthics, anti-inflammatory compounds, CNS stimulants, sedatives, anti-cholinergics, antiarteriosclerotics, and the like. The pharmaceutical agent may be intended for topical or systemic use. A pharmaceutical agent also includes macromolecular substances such as, without limitation, monoclonal antibodies (mabs), fabs, proteins, peptides, cells, antigens, nucleic acids, enzymes, growth factors and the like. Other biologically active substances include, without limitation, compounds useful for pest control such as herbicides, fungicides and insecticides. Still further biologically active substances that can be used with the hydrogel particles and aggregates of this invention will become apparent to those skilled in the art based on the disclosures herein. The use of any and all such substances with the hydrogel particles, aggregates and methods disclosed herein are within the scope of this invention.

An "excipient" refers to an inert substance added to a pharmaceutical composition to facilitate its administration. Examples, without limitation, of excipients include calcium carbonate, calcium phosphate, various sugars and types of starch, cellulose derivatives, gelatin, vegetable oils and polyethylene glycols. A "pharmaceutically acceptable excipient" refers to an excipient that does not cause significant irritation to an organism and does not abrogate the biological activity and properties of the administered compound.

As used herein, the term "cancer" refers to malignant neoplasms, which, in turn relate to a large group of diseases that can arise in virtually any tissue composed of potentially dividing cells. The basic characteristic of cancer is a transmissible abnormality of cells that is manifested by reduced control over growth and function leading to serious adverse effects on the host through invasive growth and metastases.

As used herein, "coronary artery disease" refers to a narrowing of the coronary arteries cause by atherosclerosis that, when sufficiently severe, limits, or, in its most serious form completely occludes, the flow of blood to the myocardium (heart muscle).

As used herein, a "respiratory disease" refers to a disease in which the lungs do not work properly so that breathing is affected. Examples, without limitation, of respiratory diseases are asthma, tuberculosis, cystic fibrosis and pneumonia.

As used herein, an "infectious disease" refers to any disease transmitted by a microorganism such as, without limitation, a bacterium, a virus, a prion, a fungus, an amoeba or a protozoon. In general, infectious diseases are communicable in nature and may be transmitted from one individual to another and are capable of producing serious illness in the other individual.

As used herein, the phrase "useful for the treatment of" means that the pharmaceutical agent is known to inhibit, preferably destroy, the causal agent of the indicated disease, disorder or condition, or to at least ameliorate its symptoms. With regard to cancer, the agent is known to at least increase the lifespan of an affected individual.

As used herein, the term "about" means ±15% of the value modified with the term.

Discussion

The shape-retentive hydrogel aggregates of this invention should find use in a host of applications including, without limitation, as controlled release vehicles for chemical compounds such as agrochemicals, pharmaceuticals and the like, as adjuncts, e.g., coatings on medical devices and as medical devices per se, as tissue growth matrices and as tissue replacement materials. The aggregates, which can be constructed of biologically inert polymers and which can absorb large quantities of water, are particularly useful for in vivo applications.

The aggregates of this invention may be formed by creating the hydrogel particles in situ or by mixing pre-formed hydrogel particles in one or more liquid(s). In either case, the liquid(s) is/are absorbed by the individual particles and then excess liquid is removed by, without limitation, vacuum drying, air evaporation or centrifugation until the particles are drawn so close together that their circumferences essentially touch and the only non-absorbed liquid remaining is that in the voids between the particles. The aggregates realize their characteristic shape-retentiveness by virtue of strong inter-particle attractive forces such as, without limitation, hydrogen bonds, and by virtue of hydrogen bonding between the particles and the liquid in the voids between the particles.

The chemical composition of the polymers, making up the individual hydrogel particles can be manipulated such that aggregates of them are very stable and do not readily degrade under environmental or physiological conditions. Or the chemical composition of the particles can be such that aggregates of them do degrade under certain conditions in a predictable and controllable fashion. For example, without limitation, by selecting the appropriate hydrogel particle composition, which will become apparent from the disclosures herein, aggregates that decompose under various conditions of temperature, pH, ionic strength, electric current and the like, can be constructed. In addition to manipulating the composition of the hydrogel particles themselves, excipients can be entrapped in the aggregate matrix during its formation. The excipients can be selected such that aggregates containing them will degrade as the excipients change structure, composition and/or reactivity upon exposure to a variety of environmental and/or physiological conditions. Excipients can also be added to imbue the resulting aggregate with a variety of different properties such as, without limitation, mechanical, optical, conductive or cosmetic properties.

In an embodiment of this invention, hydrogel particles, having nominal diameters in the $10^{-9}$ meters (m, nano scale) to the $10^{-6}$ m (micro scale) range are produced by redox, free radical or photo-initiated polymerization in the presence of a surfactant and water. In this manner, particles of relatively narrow polydispersivity, i.e., narrow range of diameters, can be produced. While narrow polydispersivity is a presently preferred embodiment of this invention, for some applications, which will become apparent to those skilled in the art based on the disclosures herein and which are within the scope of this invention, a broader polydispersivity may be desirable.

The resulting aqueous suspension of hydrated hydrogel particles may be treated to remove unreacted monomers and surfactant from the water absorbed by the particles. The treatment may include, without limitation, dialysis, extraction or tangential flow filtration. Simultaneously, unreacted monomer and surfactant can be removed from the non-absorbed water in which the particles are suspended. The suspension of purified particles is then centrifuged to remove excess water and compact the particles into the shape-retentive aggregate of this invention. An advantage of using nano- or micro-size particles is that they have a high surface area to volume ratio and can be relatively easily purified.

Preferred classes of monomers useful in the preparation of the hydrogel particles and subsequent aggregates of this invention include, without limitation, hydroxyalkyl 2-alkenoates such as the hydroxy(2C-4C)alkyl methacrylates and the hydroxy(2C -4C)alkyl acrylates; the hydroxy((2C-4C)alkoxy(2C.-4C)alkyl) alkenoates such as 2-hydroxyethoxyethyl acrylate and methacrylate; the (1C-4C)alkoxy(1C-4C)alkyl methacrylates, e.g., ethoxyethyl methacrylate; the 2-alkenoic acids, such as acrylic and methacrylic acid; the (1C-4C)alkoxy(2C-4C)alkoxy(2C-4C)alkyl) alkenoates such as ethoxyethoxyethyl acrylate and methacrylate; the N-vinylpyrrolidones such as the N-mono- and di-(1C-4C) alkyl vinylpyrrolidones; the 2-alkenamides such as the N-(1C -4C) alkyl-2-alkenamides and N,N-di(1C-4C)alkyl-2-alkenamides, for example, the N-(1C-4C)alkylacrylamides, the N-(1C-4C)alkylmethacrylamides, the N,N-di(1C-4C)alkylacrylamides and the N,N-di(1C-4C) alkylmethacrylamides; the dialkylaminoalkyl 2-alkenoates, e.g., diethylaminoethyl acrylate and methacrylate; the vinylpyridines; the vicinal-epoxyalkyl 2-alkenoates such as the vicinal epoxy(1C-4C)alkyl)methacrylates and the vicinal epoxy(1C-4C)alkyl acrylates, and combinations thereof. Other monomers capable of hydrogen-bonding will become apparent to those skilled in the art based on the disclosures herein and are within the scope of this invention.

Non-polymerizing excipients such as, without limitation, the alkyl alkanoates, e.g., methyl butyrate, butyl acetate, etc. may be added to the polymerization reaction to modify the physical and chemical characteristics of the resulting hydrogel particles.

Presently preferred monomers include 2-hydroxyethyl acrylate, 2-hydroxyethyl methacrylate, diethylene glycol monoacrylate, diethylene glycol monomethacrylate, 2-hydropropyl acrylate, 2-hydroxypropyl methacrylate, 3-hydroxypropyl acrylate, 3-hydroxypropyl methacrylate, dipropylene glycol monomethacrylate, dipropylene glycol monoacrylate, glycidyl methacrylate, 2,3-dihydroxypropyl methacrylate, and the like. Presently, the most preferred monomer is 2-hydroxyethyl methacrylate (HEMA).

Examples of presently preferred co-monomers used in conjunction with the above preferred monomers are acrylamide, N-methylmethacrylamide, N,N-dimethacrylamide, methylvinylpyrrolidone, N,N-dimethylaminoethyl methacrylate N,N-dimethylaminoethyl acrylate, acrylic acid and methacrylic acid.

If desired, a cross-linking agent may be added to the polymerization reaction to strengthen the three-dimensional structure of the resulting hydrogel particles. The cross-linking agent can be non-degradable, such as, without limitation, ethylene glycol diacrylate or dimethacrylate, 1,4-butylene dimethacrylate, diethylene glycol dimethacrylate, propylene glycol dimethacrylate, diethylene glycol dimethacrylate, dipropylene glycol dimethacrylate, diethylene glycol diacrylate, dipropylene glycol diacrylate, divinyl benzene, divinyltoluene, triallyl melamine, N,N'-methylene bisacrylamide, diallyl maleate, divinyl ether, diallyl monoethylene glycol citrate, vinyl allyl citrate, allyl vinyl maleate, divinyl sulfone, hexahydro-1,3,5-triallyltriazine, triallyl phosphite, diallyl benzene phosphonate, a polyester of maleic anhydride with triethylene glycol, diallyl aconitrate, divinyl citraconate, trimethylolpropane trimethacrylate and diallyl fumarate. Other non-degradable cross-linking agents will become apparent to those skilled in the art based on the disclosures herein and are within the scope of this invention. Other methods of achieving a three-dimensional polymeric network that are well-known in the art may be used in preparing the hydrogel particles and aggregates of this invention and all such methods are within the scope of this invention.

The cross-linking agent may be selected such that it is degradable under selected conditions, if such is desired for the intended use. Examples without limitation, of degradable cross-linking agents include diallyl tartrate, allyl pyruvate, allyl maleate, divinyl tartrate, diallyl itaconate and ethylene glycol diester of itaconic acid.

A presently preferred class of degradable cross-linking agents is provided in U.S. patent application Ser. No. 091338,404, which is incorporated by reference, including any drawings, as if fully set forth herein. These cross-linkers are monomers or oligomers comprised of a molecule having at least two carboxyl groups and at least two cross-linking functional groups. Between at least one of the cross-linking functional groups and one of the carboxyl groups is a degradable poly(hydroxyalkyl acid ester) sequence of 1-6 repetitions.

In another embodiment, aggregates of this invention are prepared from bulk hydrogel polymers. The bulk polymer is prepared by conventional polymerization techniques such as, without limitation, solution, suspension and aqueous bulk polymerization and the resultant polymer is isolated, treated to remove residual monomer and any other undesirable materials and dried. The dry, brittle bulk polymer is broken up by grinding, micropulverizing and the like, and the fragments are sieved using techniques known in the industry. Particles of the desired size range are stirred in a selected liquid or liquids until they have absorbed the desired amount of liquid.

Preferred liquids for use in this invention are chemically, particularly biologically, inert, non-toxic, polar, water-miscible organic liquids such as, without limitation, ethylene glycol, propylene glycol, dipropylene glycol, butanediol-1,3, butanediol-1,4, hexanediol-2,5,2-methyl-2,4-pentanediol, heptanediol-2,4, 2-ethyl-1,3-hexanediol, diethylene glycol, triethylene glycol, tetraethylene glycols, and the higher polyethylene glycols and other water-soluble oxyalkylene homopolymers and copolymers having a molecular weight up to 2000, and higher, preferably up to 1600. For example, hydroxy-terminated polymers of ethylene oxide having average molecular weights of 200-1000, the water-soluble oxyethyleneoxypropylene polyol (especially glycol) polymers having molecular weights up to about 1500, preferably up to about 1000, propylene glycol monomethyl ether, monoacetin, glycerine, tri(hydroxyethyl) citrate, ethylene glycol monomethyl ether, ethylene glycol monoethyl ether, di(hydroxypropyl) oxalate, hydroxypropyl acetate, glyceryl triacetate, glyceryl tributyrate, liquid sorbitol ethylene oxide adducts, liquid glycerine ethylene oxide adducts, diethylene glycol monomethyl ether, diethylene glycol monoethyl ether, and ethylene glycol diacetate may be used. Other hydroxy and hydroxy/ether liquids capable of hydrogen bonding with the hydrogel particles will become apparent to those skilled in the art based on the disclosures herein and are within the scope of this invention.

In a presently preferred embodiment of this invention, the organic liquid(s) has/have boiling points above about 60° C., preferable above about 200° C. The use of these liquids results in the formation of intricate, tough aggregates. Thus, organic liquids that are particularly useful in forming the aggregates of this invention are the water-miscible oxyalkylene polymers, e.g., the polyalkylene glycols, especially those characterized by a plurality of oxyethylene ($-OCH_2CH_2-$) units in the molecule and a boiling point above about 200° C.

Criteria which will affect the chemical and physical characteristics of the aggregates of this invention include the molecular weight of the polymer forming the individual hydrogel particles, the particle size, the cross-linking agent, if any, and its cross-linking density, and the molecular weight and chemical composition of the liquids used. For example, hydrogel particles consisting of low molecular weight polymers will generally not form stable, strong aggregates. Smaller hydrogel particles will generally provide aggregates that are thoroughly and effectively solvated, resulting in a more resilient matrix. If the hydrogel polymer contains a large amount of cross-linking agent and/or if the cross-linking agent is highly hydrophobic, the resulting branched polymeric network may not permit optimal absorption of liquid resulting in inferior aggregates and in some cases no aggregates result.

In an embodiment of the present invention, nano- or micro-size hydrogel particles are produced by polymerizing non-ionic monomers in water containing a surfactant. The suspension of hydrogel particles is treated to remove unreacted monomer and other impurities. Aggregates are then formed by removing water until the particles self-assemble into a compact elastic matrix. The aggregate can then be, without limitation, pressure shaped, extruded, or molded. The aggregate will retain the shape indefinitely so long as it is maintained in the hydrated state.

In another embodiment of the present invention, monomers having various degrees of ionic character are co-polymerized with non-ionic monomers to form hydrogel particles that are subsequently coalesced into aggregates. These aggregates are susceptible to decomposition under the appropriate environmental conditions. That is, the ionic character of the individual hydrogel particles can result in their degradation depending on the pH, temperature, ionic strength, electric current, etc. of their immediate environment. Breakdown of the hydrogel particles leads to degradation of the aggregate. Such controlled degradation of aggregates of this invention is a desirable characteristic for certain uses.

Breakdown of the individual hydrogel particles and thereby breakdown of the aggregate may also be accomplished by using degradable cross-linking agents in the formation of the hydrogel particles. The resulting aggregate will dissemble under environmental conditions that cause degradation of the cross-linker. Cross-linking agents can be prepared that will degrade under selected conditions of, without limitation, pH, temperature, ionic strength and electric current.

The aggregates of this invention have many uses, among which the delivery of biologically active substances to a selected target is particularly noteworthy. The target may be agricultural, such as, without limitation, the delivery of a fungicide, insecticide or herbicide to a commercial crop; e.g. corn, cotton, soy beans, wheat, etc. Or, the target may be the growth medium, e.g., the soil, in which the crop is growing and may involve the delivery of nutrients and the like. The target may be environmental contaminants in soil, which contaminants may be controllably degraded using aggregates of this invention. The target may be veterinary, involving delivery of medicaments to animals such as reptiles, mammals and birds. In particular, the target may be a human involving the controlled, directed delivery of pharmaceutical agents to the patient.

The delivery of biologically active substances using aggregates of this invention can be accomplished primarily in two ways, and combinations thereof. The first approach involves dissolving or suspending the biologically active material in a suspension of hydrated hydrogel particles before the excess liquid is removed to create an aggregate. A water-soluble substance is preferred to ensure homogeneity of the bulk liquid before concentration. However, adjuvants, such as surfactants, can be added to the mix to render a suspension of a limited solubility biologically active substance relatively homogeneous. As the suspension is concentrated to the point that an aggregate forms, the biologically active substance becomes entrapped in the liquid that fills the voids between the particles of the aggregate. The resulting resilient, shape-retentive aggregate can be washed to remove any biologically active substance adhered to its surface. The aggregate can then be shaped for the intended use, if desired. For example, without limitation, if the contemplated use is treatment of an infection, the aggregate could be shaped to fit directly into a wound and to release an antibiotic therein. Likewise, if the use is delivery of a chemotherapeutic, such as, without limitation, paclitaxel or cisplatin, to a target organ in a cancer patient, the aggregate could be shaped to facilitate implantation at the afflicted site.

The second approach involves dissolving or suspending the biologically active substance in the polymerization medium before formation of the hydrogel particles. When polymerization is initiated and the particles form, liquid containing the biologically active substance is entrapped within the individual particles. When the particles are treated as discussed above to remove excess monomer and surfactant, excess biologically active substance not trapped within the particles will also be removed. The suspension of biologically active substance-containing particles is then concentrated until the particles coalesce into an aggregate.

As noted above, it is possible to combine the two approaches. That is, rather than removing the biologically active substance with the excess monomer and surfactant before concentration of the hydrogel particle suspension, the active substance can be left in the suspension liquid. In this manner, the resulting aggregate will have biologically active substance entrapped both within the individual hydrogel particles and in the voids between the particles. On the other hand, the suspension of hydrogel particles can be purified as above and then the biologically active substance or, if desired, an entirely different biologically active substance can be re-introduced into the mixture before concentration. The substance in the voids in the aggregate will normally be released at a very different rate from the substance in the particles. In this manner, a broad range of delivery profiles and rates and be achieved. Diversity can also be achieved by varying the chemical composition of the individual hydrogel particles of the aggregate.

If no chemical modification is incorporated into the individual hydrogel particles such as, without limitation, ionic character or the use of degradable cross-linkers, the aggregate will be essentially impervious to normal environmental conditions. This type of aggregate will generally provide release rates similar to monolithic matrix devices, that is, an initial burst of substance followed by an exponential drop off with time. However, if the hydrogel particles are designed such that they degrade under the environmental conditions encountered at the delivery site and if the biologically active substance will be released from the aggregate only upon disintegration of the particles, extremely fine control of delivery rate is possible. Assuring that active substance release will occur only upon disintegration of the hydrogel particles can be accomplished by using particles of a size that will result in an aggregate having pores too small for the entrapped active substance to traverse when the aggregate is intact. Likewise, the individual particles can be formed such that active substance entrapped within them cannot escape absent particle disintegration.

In addition to the above, water soluble adjuncts may be added to the aggregates to alter disintegration rate and, therefore, the release rate of the entrapped active substance. Furthermore, particles comprising cationic and/or anionic charges can be mixed with non-ionic hydrogel particles to provide controlled disintegration of the aggregates under a variety of conditions including the ionic character of the environs or the existence of an external electric charge. The inclusion of charged species may also increase aggregation efficiency due to electrostatic charge interaction.

Using one or more of the above procedures, zero-order, or at least pseudo-zero order, release rates should be attainable.

The type and amount of a substance that can be entrapped in a hydrogel particle or aggregate of this invention depends upon a variety of factors. The substance cannot interfere, due to its size, surface charges, polarity, steric interactions, etc., with the coalescence of the hydrogel particles into an aggregate. The size of the hydrogel particles will affect the quantity of substance that can be incorporated. That is, by appropriate selection of particle size, the resulting aggregate pore size can be manipulated so as to retain small substances, such as individual antibiotic molecules or very large substances such as monoclonal antibodies, proteins, peptides, or other macromolecules.

Using the methods herein, exquisite control of substance delivery, in particular delivery kinetics, should be attainable. That is, hydrogel particles of differing sizes and chemical compositions could be loaded with a particular substance and, depending on the degradation characteristics of the various particles, the substance could be released over virtually any desired timeframe. In addition, some of the substance could be encased in the hydrogel particles and some could be trapped in the voids between particles of the aggregate to provide even more delivery flexibility. Different substances, even those normally incompatible, could be loaded into different types of particles and sequentially or simultaneously released. Sequential release would prevent the incompatible substances from encountering one another while simultaneous release would allow them to interact at the release site. This latter scenario could be particularly useful in the case of two or more non- or minimally bioactive substances that, when combined, form an extremely potent drug. The formation of the active drug could be postponed until an aggregate containing the precursors has been delivered to the site where the effect of the drug is required thereby minimizing side effects.

Thus, the present invention provides an extremely versatile drug delivery platform. A drug or combination of drugs may be delivered over an extended time period. A combination of drugs may be delivered sequentially so that one has its effect and dissipates before the next is released. A combination of drugs may be released simultaneous to synergistically interact. Other uses will become apparent to those skilled in the art based on this disclosure; such uses are within the scope of this invention.

Another area of potential utility for the aggregates of this invention is tissue scaffolding. The macroporous structure of the aggregates provides a composition that will allow substantial ingrowth, a property not found in typical microporous bulk hydrogels. In addition, the aggregates herein exhibit physical properties such as elastic, shear and bulk moduli that are significantly greater than those of conventional bulk hydrogels, approaching in some cases the properties of articular cartilage. Furthermore, the ability to mold and layer the aggregates of this invention could be used to optimize the release of growth factor at specific locations within a tissue scaffold. Possible orthopedic applications include cartilage and bone repair, meniscus repair/replacement, artificial spinal discs, artificial tendons and ligaments, and bone defect filler.

The shape retentive property of the aggregates herein suggests numerous other in vivo uses. For example, a medicated or unmedicated aggregate could be molded into a soft contact lens. A wound dressing or skin donor site dressing, with or without incorporated antibiotics or other drugs, could be fabricated from the present aggregates. An aggregate could be formed into an in-dwelling medicated or non-medicated catheter or stent. Numerous other such uses will become apparent to those skilled in the art based on the disclosure herein and are within the scope of this invention.

Other uses for the aggregates of this invention include using a mixture of particles, some of which will degrade over a predetermined time interval, in applications that require a change in material morphology with time. Also, aggregates composed of a mixture of hydrogel particles and other types of particles, such as metals, radioactive particles, semiconductors, non-hydrogel-forming polymers, ceramics, colorants, UV and IR filters, radiopaque materials, and the like.

For example, without limitation, metals could be entrapped in the hydrogel particles, in the voids in the aggregate or both. The metals would confer varying degrees of conductivity on the aggregates. The metals may also be incorporated as ions, that is, metals in oxidation states other than zero. Once again, these ions can also confer degrees of conductivity on the aggregates. To the contrary, the hydrogel particles or the aggregates may be infused with semiconductor metals or compounds. Shape retentive semiconductor aggregates or even aggregates with some hydrogel particles that are semi-conducting by virtue of incorporation of semiconductor materials and some of which are conducting by incorporation of metals should find use in MEMS (MicroElectroMechanical System) and NEMS (NanoElectroMechanical System) devices. Entrapment of magnetic materials such as magnetic polymers or magnetic metal particles could afford a three dimensional computer memory device. Incorporation of polynucleotide segments in the particles of an aggregate could lead to three-dimensional array analytical tools for use in the biotechnology industry. These and may other uses for the shape-retentive aggregates of this invention will become apparent to those skilled in the art based on the disclosures herein. Such uses are within the scope of this invention.

EXAMPLES

Example 1

Preparation of Crosslinked HEMA Nanoparticles

A 500 mL media bottle equipped with a stir bar was charged with 4.52 g (34.8 mmol) HEMA monomer, 77.74 mg (0.428 mmol) ethylene glycol dimethacrylate (EGDM), 0.2123 g (0.634 mmol) sodium dodecyl sulfate (SDS) and 240 mL milli-Q $H_2O$. The bottle was closed with a sparging cap and purged with $N_2$ for 1 hr at room temperature while stirring. Then, 0.166 g $K_2S_2O_8$ was dissolved into 21 mL of milli-Q $H_2O$ and added to the media bottle while stirring. The bottle was transferred to a 40° C. water bath and held there for 12 hours. The resulting suspension of hydrogel particles had an opalescent blue color. The particles were analyzed by dynamic light scattering and found to have an average radius of 36.5 nm as shown in FIG. 1. The particles were purified by tangential flow filtration and are stored in an aqueous suspension. No flocculation was observed over several months.

Example 2

Size Variation of HEMA Nanoparticles

Figure 2:
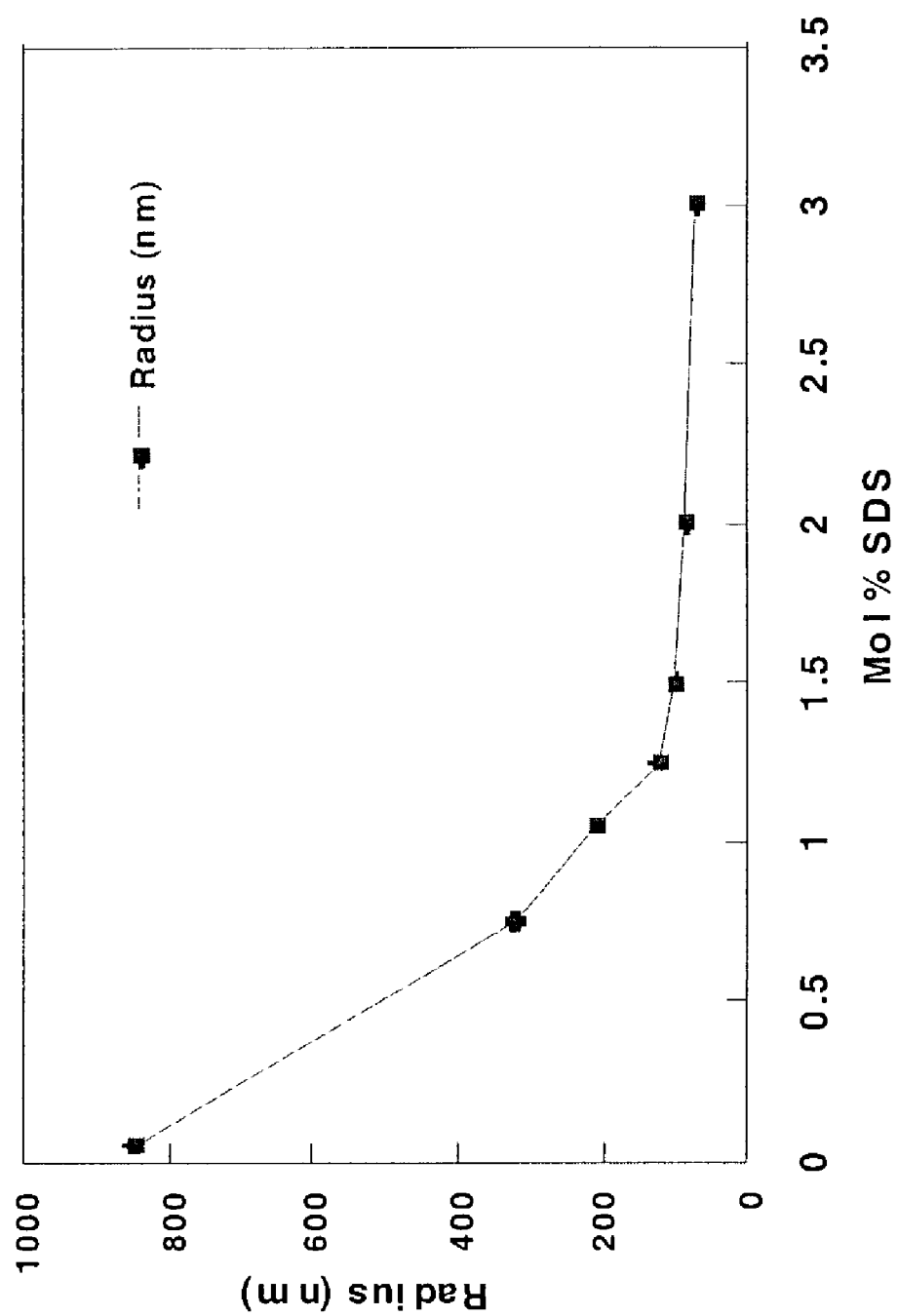
FIG. 2 is a graph of the radius of polyHEMA hydrogel particles formed by the polymerization method of this invention as a function of the mol percent of surfactant employed in the reaction.
Figure 3:
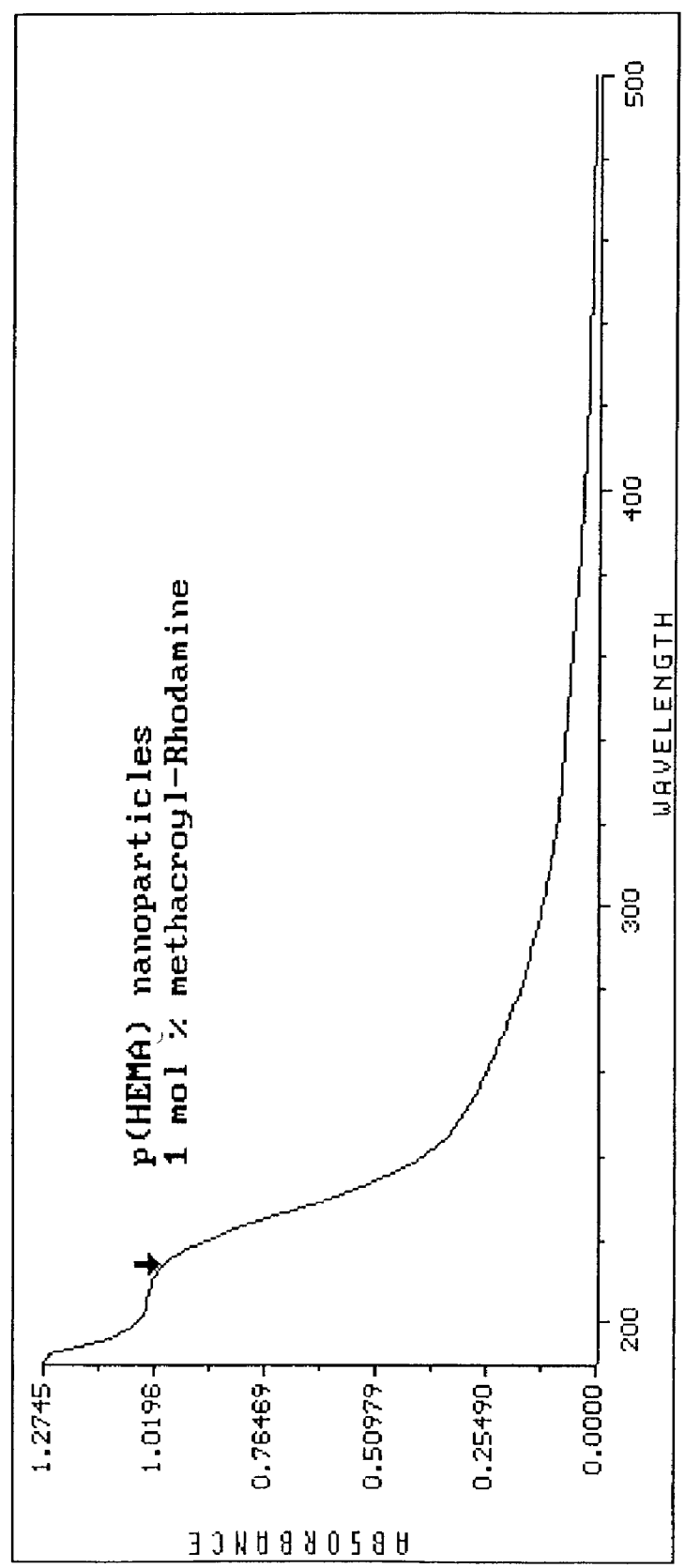
FIG. 3 shows the UV-visible absorption spectrum obtained from poly (HEMA-co-1% methacroyl Rhodamine-B) hydrogel particles.
Figure 4:
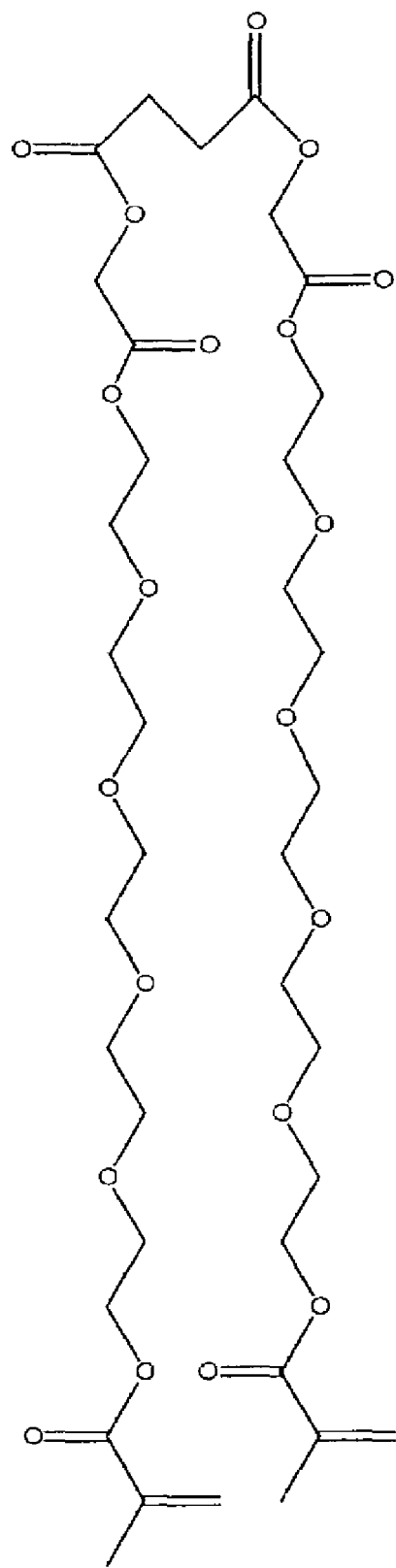
FIG. 4 shows the chemical structure of (methacroyl (polyethylene glycol) $_{3-4}$glycolyl)$_2$ succinate (MA-pEG$_{3-4}$-Gyl)$_2$Suc degradable cross-linking agent.

Following the procedure of Example 1, the ratio of monomers to surfactant was varied. An increase in the ratio of monomer to surfactant resulted in the formation of larger particles during polymerization as evidenced by laser light scattering. The size variation of HEMA particles with changes in mole percent SDS surfactant is shown in FIG. 2.

Example 3

Incorporation of Co-Monomer in HEMA Nanoparticles

A 250 mL media bottle equipped with a stir bar was charged with 2.22 g (16.53 mmol) HEMA monomer, 74.9 mg (0.87 mmol) MM, 38.87 mg (0.214 mmol) ethylene glycol dimethacrylate (EGDM), 0.107 g (0.317 mmol) sodium dodecyl sulfate (SDS) and 120 mL milli-Q $H_2O$. The bottle was closed with a sparging cap and purged with $N_2$ for 1 hr at room temperature while stirring. Then, 0.083 g $K_2S_2O_8$ was dissolved in 10.5 mL milli Q $H_2O$ and added to the media bottle while stirring. The bottle was transferred to a 40° C. water bath and left there for 12 hours. The particles that formed were purified by tangential flow filtration. Methacrylic acid was incorporated at 5, 10, 20, and 30 mole percent of the total monomers and at different concentrations of sodium dodecyl sulfate. Table 1 shows the change in particle size with varying concentrations of methacrylic acid and varying buffer pH.

TABLE 1

| Mole % MAA | PH = 5 | pH = 7.4 | pH = 11 |
| --- | --- | --- | --- |
| 5 mol % MAA | 52.5 nm | 67.3 nm | 81.1 nm |
| 10 mol % MAA | 61.3 nm | 78.1 nm | 100.3 nm |
| 20 mol % MAA | 91.3 nm | 118.5 nm | 141.3 nm |

Using the synthetic method of Example 1, other co-monomers were polymerized with HEMA to form hydrogel particles including 2-aminoethylmethacrylate.HCl, trimethylaminoethyl-methacrylate HCl, and methacroyl rhodamine-B fluorescent monomer. Table 2 shows the relative sizes determined by light scattering for HEMA-comonomer particles synthesized at differing pH:

TABLE 2

| Mole % co-monomer | PH = 5 | pH = 7.4 | pH = 11 |
| --- | --- | --- | --- |
| 15 mol % trimethylaminoethyl methacrylate•HCl | 234.5 nm | 33.18 nm | precipitate |
| 15 mol % 2-aminoethyl methacrylate•HCl | 188.1 nm | 178.1 nm | 115.4 nm |

FIG. 2 shows the U-Visible spectrum of HEMA nanoparticles containing 1 mol % comonomer methacroyl rhodamine b (Polyfluor 540®). The broad absorption band at 340 nm is characteristic for excitation of Rhodamine-B. The nanoparticles also exhibit orange fluorescence under UV-excitation.

Example 4

Formation and Characterization of Degradable HEMA Nanoparticles

A 250 mL media bottle equipped with a stir bar was charged with 2.22 g (16.53 mmol) HEMA monomer, 74.9 mg (0.87 mmol) methacrylic acid, 167 mg (0.214 mmol) (MA-pEG$_{3-4}$Gly)$_2$Suc, 0.107 g (0.317 mmol) sodium dodecyl sulfate (SDS) and 120 mL milli-Q H$_2$O. The bottle was closed with a sparging cap and purged with N$_2$ for 1 hr at room temperature while stirring. Then, 0.083 g K$_2$S$_2$O$_8$ was dissolved in 10.5 mL milli Q H$_2$O and added to the media bottle while stirring. The bottle was transferred to a 40° C. water bath and left there for 12 hours. The solution exhibited an opalescent blue color. The hydrogel particles were characterized by light scattering and had an average radius of 68.4 nm.

Figure 5:
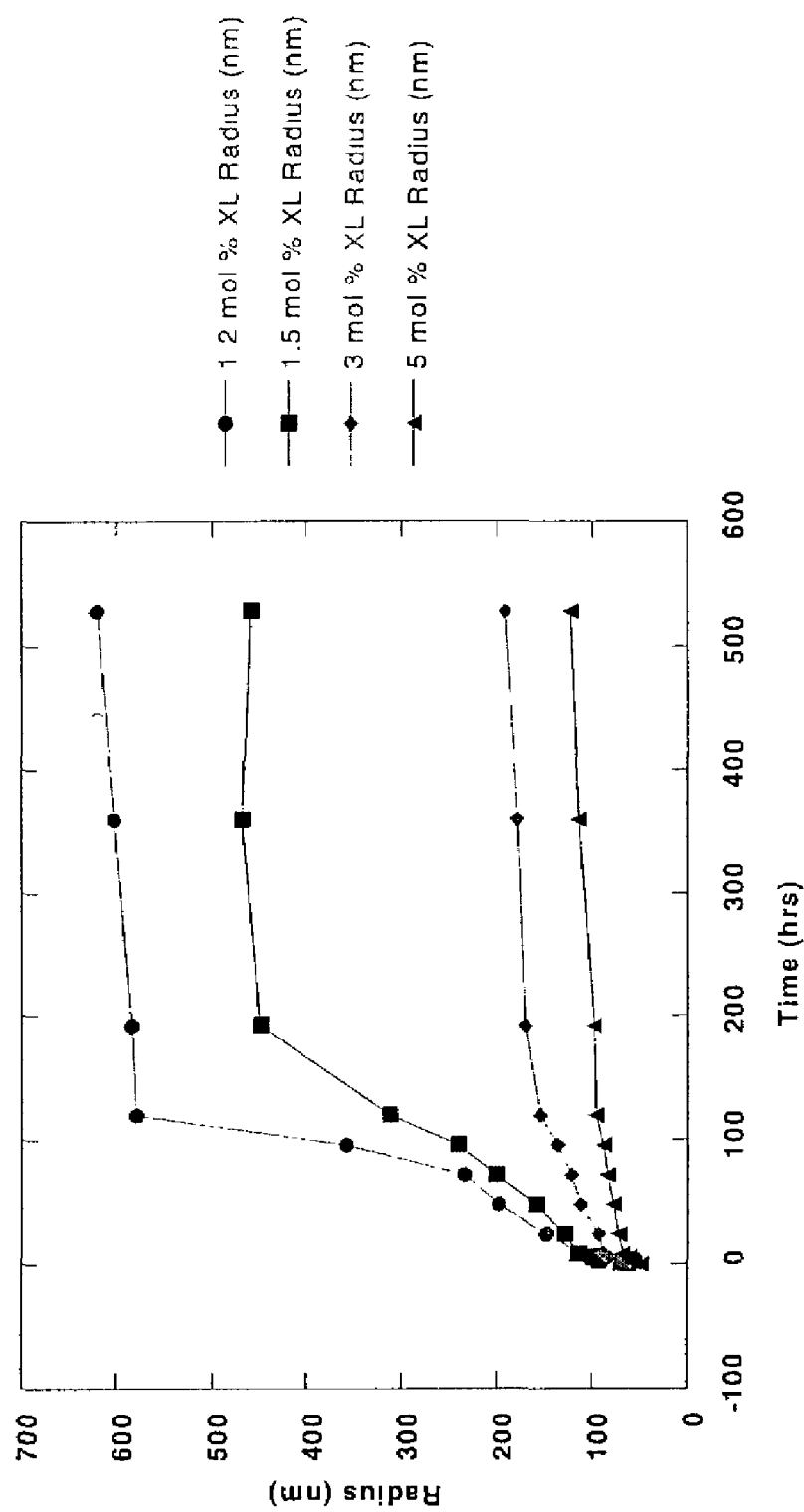
FIG. 5 shows the degradation over time of poly(HEMA-co-MM) hydrogel particles cross-linked with (MA-pEG$_{3-4}$-Gly)$_2$Suc at 37° C. and pH 7.4.

Particle degradation was studied by observing the change in size over time at a given pH and temperature. A typical degradation study involved a solution of hydrogel particles at a concentration of 0.1 mg/mL in phosphate buffered saline (120 mmol chloride) at pH 7.4 incubated at 37° C. Aliquots were removed periodically and the average radius of the particles was determined by dynamic light scattering. A plot showing the change in radius of HEMA-co-MAA particles with different degradable crosslinker concentrations is shown in FIG. 5.

Example 5

Incorporation of Molecules into Hydrogel Nanoparticles During Polymerization

Bromocresol green, 2-ethylhexyltrans-4-methoxycinnamate, Pilocarpine, fluorescein-labeled bovine serum Albumin (FITC-BSA), and horseradish peroxidase (HRP) were entrapped in polyHEMA hydrogel particles. Table 3 shows the relative loading of the above compounds as percent by mass contained in poly (HEMA-co-MAA) hydrogel particles crosslinked with EGDM.

TABLE 3

| Molecule | Percent by mass |
|---|---|
| Bromocresol green | 8.4% |
| 2-ethylhexyltrans-4-methoxycinnamte | 6.3% |
| Pilocarpine | 10.4% |
| FITC BSA | 1.2% |
| HRP | 1.8% |

The amount loaded was determined by calculating the initial concentration of each compound in solution before polymerization and analyzing the concentration of each in the supernatant after polymerization.

Example 6

Formation of Nanoparticle Aggregates by Centrifugation

Figure 7:
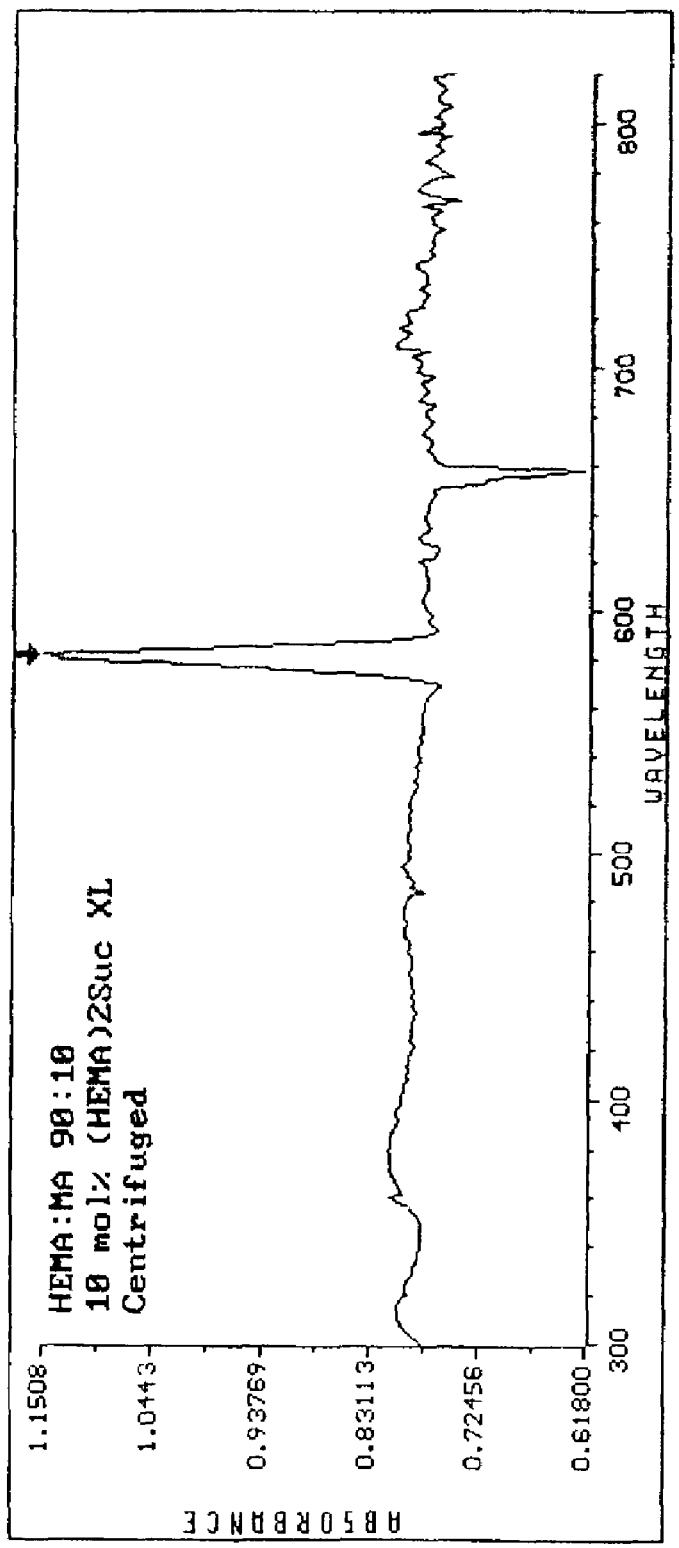
FIG. 7 shows that a thin sheet of an aggregate formed from narrow dispersivity polyHEMA hydrogel particles exhibits Bragg diffraction indicating that the aggregate has a polycrystalline-like structure.

A 0.4% (w/w) suspension of polyHEMA hydrogel particles (20 mL) was placed in a polycarbonate ultracentrifuge tube and spun at 100,000×G for 30 minutes. The hydrogel particles formed a solid plug at the bottom of the tube. The plug exhibited a blue opalescent color and was elastic. A cartoon showing the formation of such an aggregate is shown in FIG. 6. The aggregate exhibits polycrystalline diffraction when formed from nanoparticles of narrow polydispersity. FIG. 7 shows the UV-visible absorption spectrum of a thin sheet of an aggregate of HEMA hydrogel particles of 52 nm radius and a full-width half maximum of 11 nm by light scattering. The spectrum shows a sharp absorption band characteristic of a Bragg diffraction characteristic of a photonic crystalline solid.

Figure 8A:
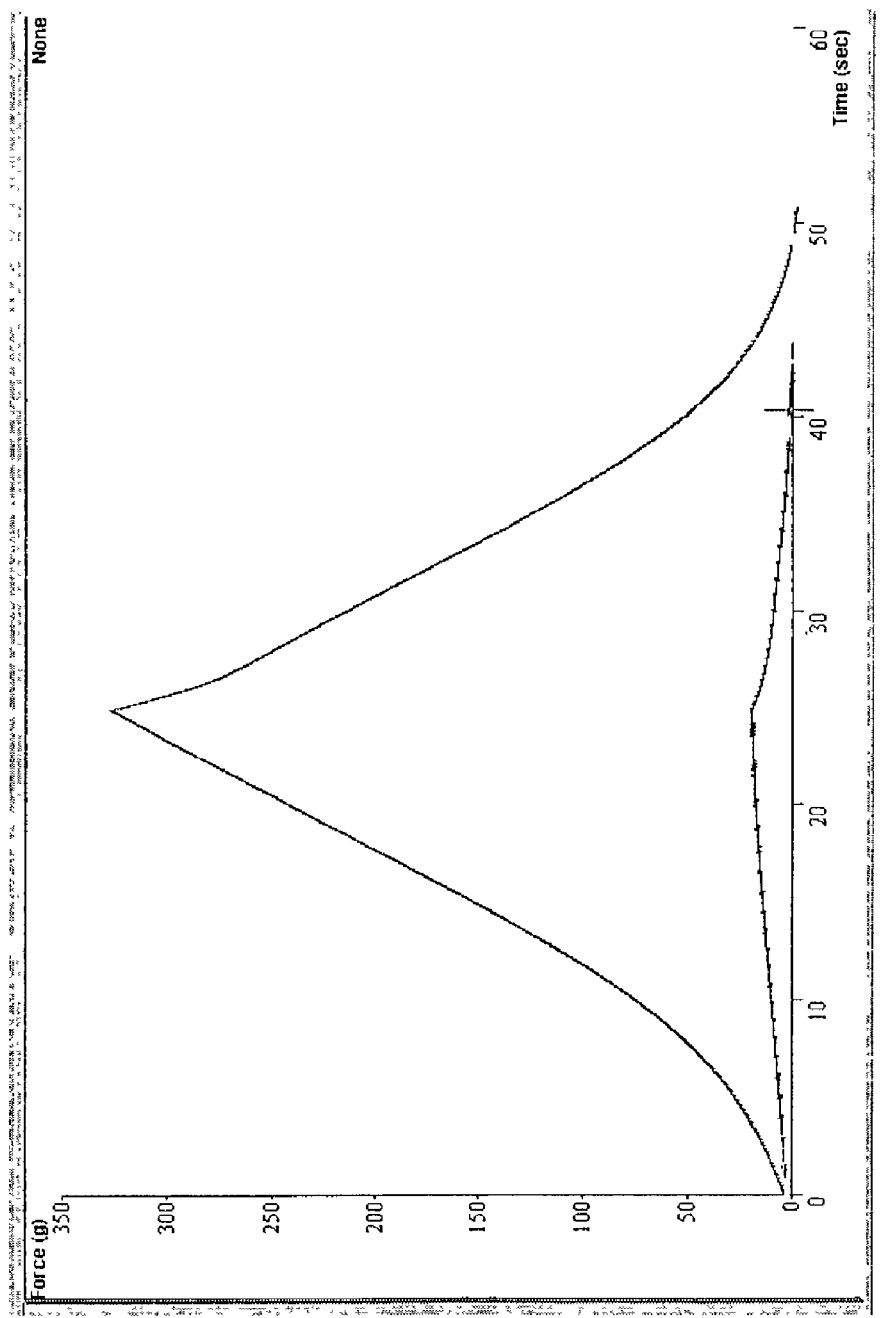
FIGS. 8A and 8B are graphic comparisons of the strain (8A) and relaxation (8B) curves of bulk polyHEMA, an aggregate of this invention comprised of polyHEMA hydrogel particles and an aggregate of this invention comprised of poly(HEMA-co-10% MM) hydrogel particles.
Figure 8B:
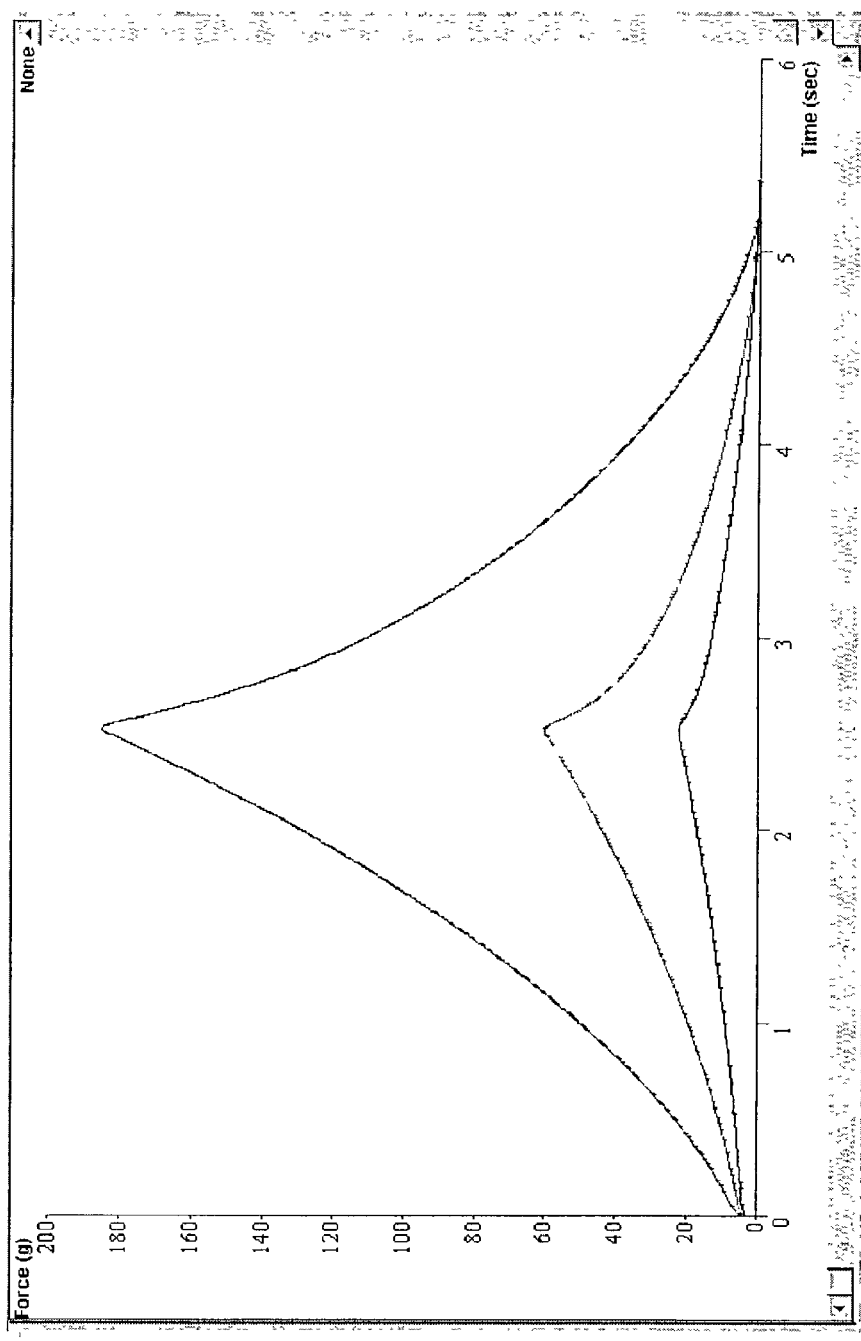

Aggregates were formed from hydrogel particles comprising a variety of co-monomers. In each case, the resulting aggregate exhibited elastic properties and strength resembling bulk cross-linked polyHEMA hydrogel. FIG. 8 shows a set of strain/relaxation curves for bulk polyHEMA, a polyHEMA nanoparticle aggregate and an aggregate composed of poly(HEMA:MAA) (90:10 molar ratio). The plots show that the bulk polyHEMA has a higher resilience and springiness than the aggregates in initial indentation studies but upon a second indentation in the same location after 10 minutes of relaxation, the aggregates show superior characteristics. Table 4 shows the stress/strain curve for the initial denting study.

TABLE 4

| Example Name | (Post Work)/ (Pre Work) Resilience ratio | (Post Travel)/ (Pre Travel) Instant Springiness ratio |
|---|---|---|
| HEMA aggregate | 0.368 | 0.473 |
| HEMA | 0.848 | 0.902 |
| HEMA:MAA Aggregate | 0.465 | 0.646 |

The above data indicate that the aggregates have approximately 50% of the resilience found in bulk polyHEMA. The energy returned over time determined by the springiness ratio was lower for the aggregates when compared to a bulk polyHEMA film. Table 5 shows the stress/strain curve for the secondary denting study after 10 minutes of relaxation.

TABLE 5

| Example Name | (Post Work)/ (Pre Work) Resilience ratio | (Post Travel)/ (Pre Travel) Instant Springiness ratio |
|---|---|---|
| HEMA aggregate | 0.641 | 0.714 |
| HEMA | 0.796 | 0.97 |
| HEMA:MAA Aggregate | 0.629 | 0.823 |

The data in table 5 indicates that the resilience and energy returned increases for aggregate films after an initial compression while the properties of the bulk HEMA film remains the same.

Example 7

Formation of Layered Nanoparticle Aggregates by Centrifugation

Ultracentrifugation of polyHEMA nanoparticles formed an aggregate with a volume of approximately 3 cm$^3$ and a mass of approximately 3.2 g. A second portion of nanoparticles composed of poly(HEMA:MAA:methacroyl rhodium B); 89:5:1 molar ratio) was centrifuged onto the first aggregate. The resulting composite aggregate appeared as a seamless bulk material with a distinct line separating the pink dye loaded particles from the underlying blue aggregate. Mechanical stimulation failed to induce separation of the two layers.

Example 8

Formation of Aggregate Thin Films by Evaporation

A thin film was formed by dispensing 30 mL of an aqueous solution of 0.1 mg/mL hydrogel nanoparticles into a 10 cm diameter shallow petri dish. The water was evaporated in air or under vacuum in a desiccator. A clear, thin film approximately 2.5 micrometers thick was formed on the dish. The film could be lifted off in one piece as an optically clear sheet. The film could be re-hydrated to form an opalescent blue film with elastic properties.

Example 9

Erosion of Non-Degradable Nanoparticle Aggregates

Figure 9:
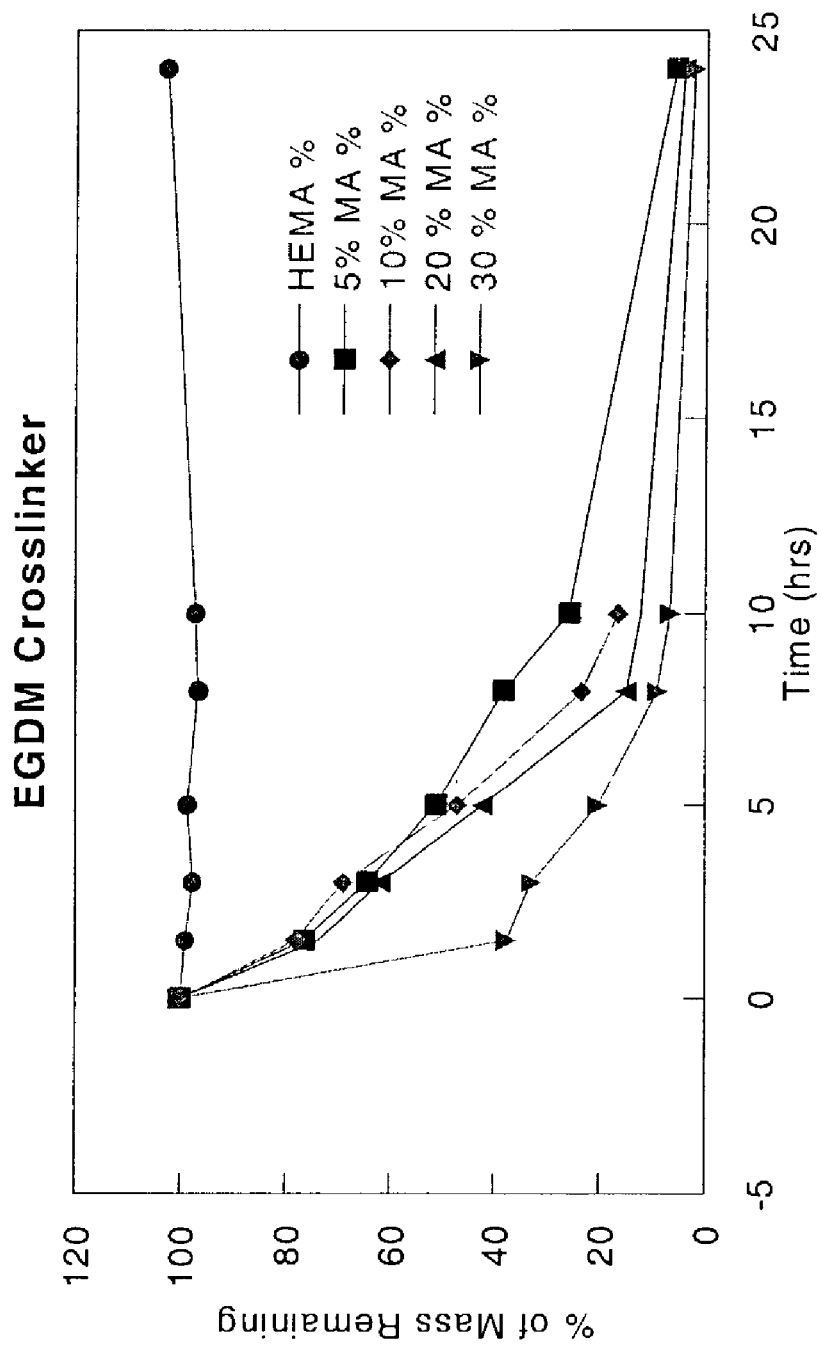
FIG. 9 is a graphic comparison of the surface erosion rate of an aggregate of polyHEMA with that of poly(HEMA-co-MM) hydrogel particles of varying MM content cross-linked with ethylene glycol dimethacrylate under 60 cycle-per-second (cps) agitation in phosphate-buffered saline (PBS) at 37° C.

An aggregate composed of poly(HEMA-MA) nanoparticles cross-linked with EGDM having a mass of 1.5 g was placed in 15 mL phosphate buffered saline (120 mmol chloride, pH 7.4) at 37° C. and was agitated on an orbital shaker at 60 cycles per second. The bulk aggregate was weighed periodically and the mass was plotted as a percentage of its initial mass. FIG. 9 shows the erosion rates for polyHEMA and poly(HEMA:MM) nanoparticle aggregates cross-linked with EGDM.

Example 10

Erosion of Degradable Nanoparticle Aggregates

Figure 10:
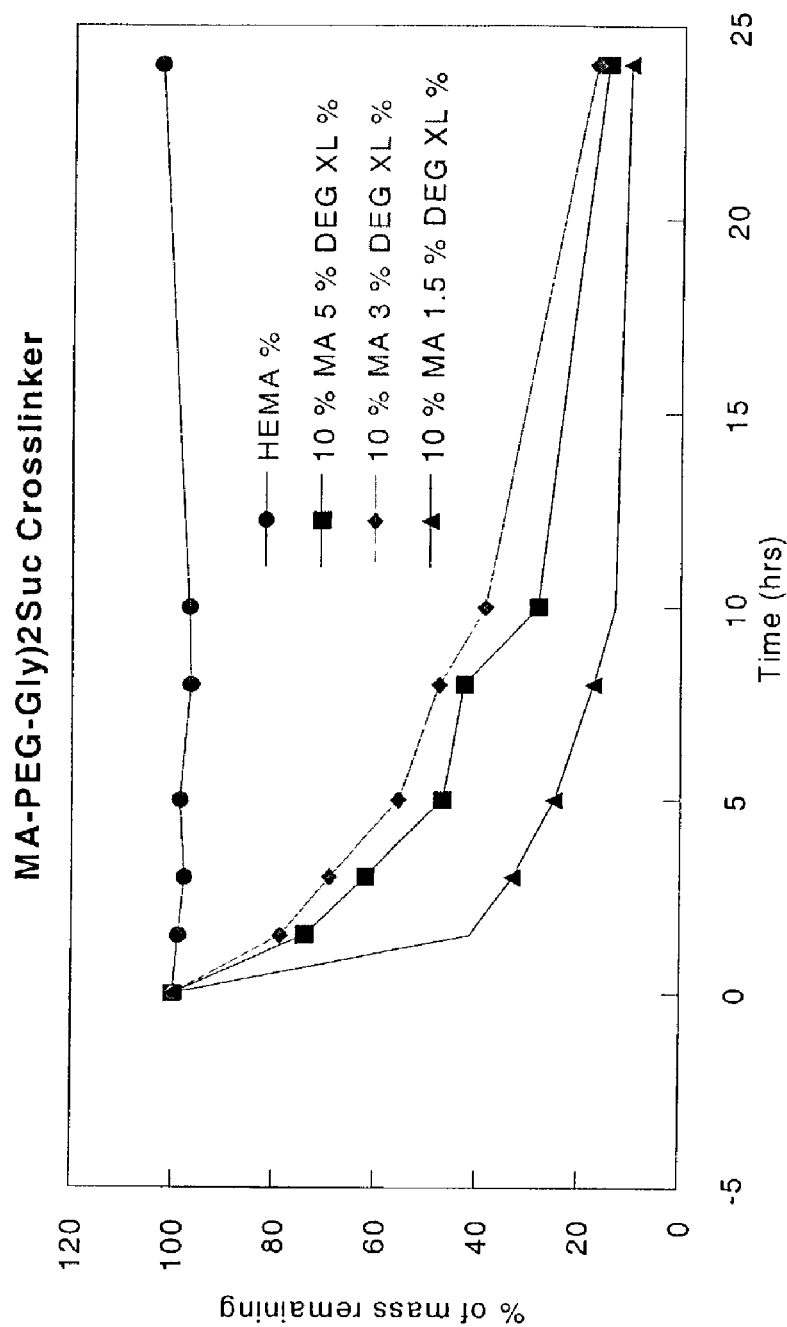
FIG. 10 is a graphic comparison of the surface erosion rate an an aggregate of polyHEMA and poly(HEMA-co-10% MAA) hydrogel particles crosslinked with (MA-pEG$_{3-4}$-Gly)$_2$ Suc under 60 cycle-per-second (cps) agitation in phosphate-buffered saline (PBS) at 37° C.

An aggregate composed of poly(HEMA:MM) (90:10 molar ratio) nanoparticles crosslinked with (MA-PEG$_{3-4}$ Gly)$_2$Suc with a mass of 1.5 g was placed into 15 mL phosphate buffered saline (120 mmol chloride, pH 7.4) at 37° C. and was agitated at 60 cycles per second on an orbital shaker. The aggregate was periodically weighed. A plot of the change in mass with time for aggregates containing varying amounts of degradable cross-linker is shown in FIG. 10.

Example 11

Incorporation of Macromolecules in the Voids Between Nanoparticles of Aggregates Large molecules of various molecular weights were trapped in the voids between nanoparticles comprising an aggregate. A solution of the macromolecule was formed at a concentration of approximately 1 mg/mL and was mixed with hydrated nanoparticles at a concentration of about 60 mg/ml. The solution was placed in a centrifuge and spun at 100,000×G for 30 min. The resulting aggregate was removed and was studied for controlled release of the macromolecule. The percent loading was determined by subtracting the concentration of macromolecule from the supernatant solution after aggregate formation from the original solution concentration. Table 6 shows the percent loading for several macromolecules.

TABLE 6

| Macromolecule | % loading by mass |
|---|---|
| FITC-BSA (66 kD) | 2.8-8.3% |
| Horseradish Peroxidase (44 kD) | 3.3% |
| FITC-Dextran (12 kD) | 14.6% |
| FITC-Dextran (19.5 kD) | 29.31% |
| FITC-Dextran (38 kD) | 12.86% |
| FITC-Dextran (456 kD) | 21.1% |

Example 12

Control of Macromolecule Release by Changes in Erosion Rate

Figure 11:
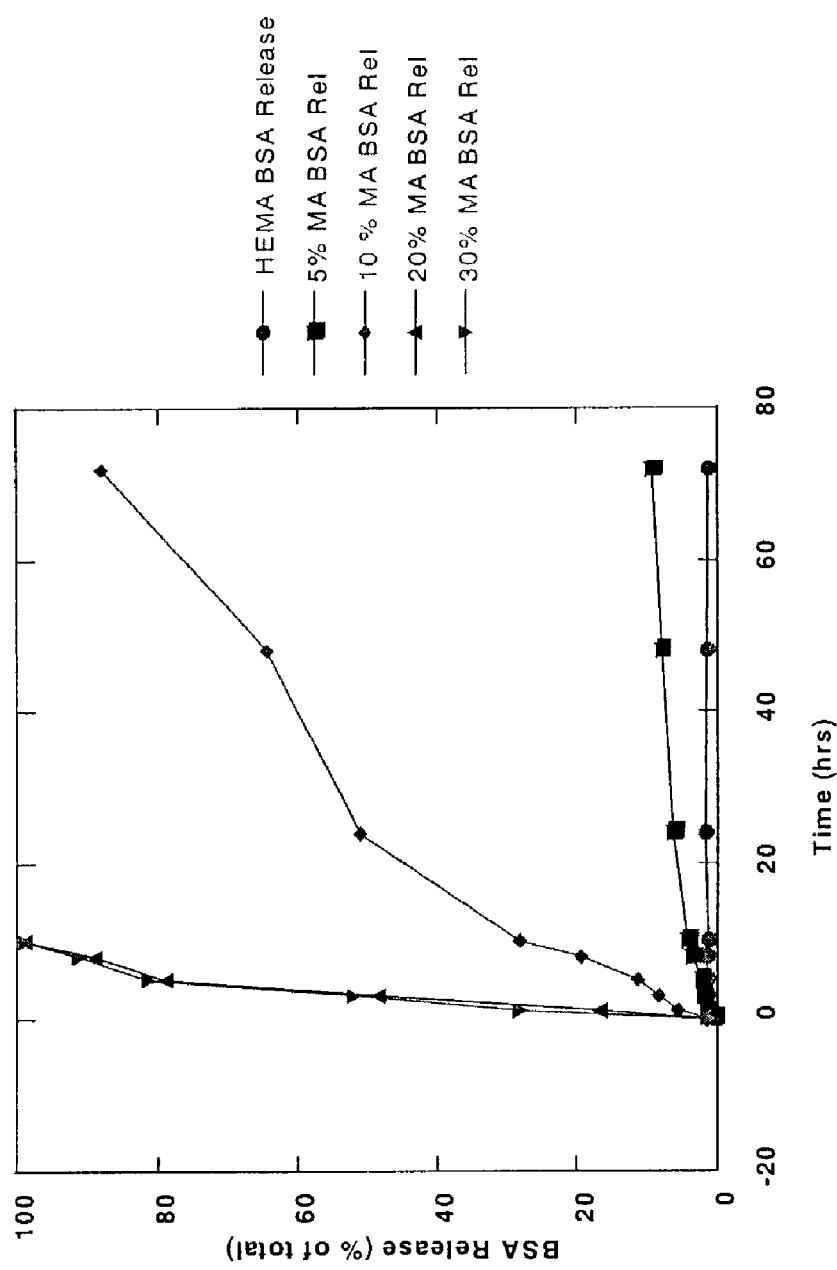
FIG. 11 is a plot of the release over time of FITC-BSA entrapped in an aggregate of poly(HEMA-co-MM) hydrogel particles under conditions consisting of 60 cps agitation in pH 7.4 PBS at 37° C.

The rate of release of a macromolecule trapped in the voids between hydrogel particles in an aggregate can be controlled by modifying the ionic character of the particles. Thus, particles were produced of approximately 40 nm diameter using 90:10 HEMA:MAA. A solution of 1 mg/mL of FITC-BSA in a suspension of 60 mg/ml hydrated copolymer nanoparticles in 20 mL milli-Q water was prepared. The solution/suspension was spun in a centrifuge at 50,000×G for 1 hr at room temperature. The resulting aggregate, which was yellow, was removed and the percent loading was determined by subtracting the FITC-BSA remaining in solution from the original solution concentration. The loading of this aggregate was calculated to be approximately 7% by weight. The aggregate was washed with five 10 mL aliquots until the washings contained no further FITC BSA as determined by UV-Visible spectroscopy. The aggregate (2.1 g) was placed in 21 mL of phosphate buffered saline (PBS, pH 7.4, NaCl concentration=120 mmol/L) at 37° C. and was shaken at 60 cycles per second on an orbital shaker. Periodic aliquots were removed and analyzed by UV-Visible spectroscopy. FIG. 11 shows the release of FITC-BSA from the aggregate over time. Variations in the mole percent methacrylic acid in the hydrogel particles of the aggregate result in distinct changes in the rate of FITC-BSA release.

Example 12

Change in Release Rate of Macromolecules of Varying Size from Aggregates

Figure 12:
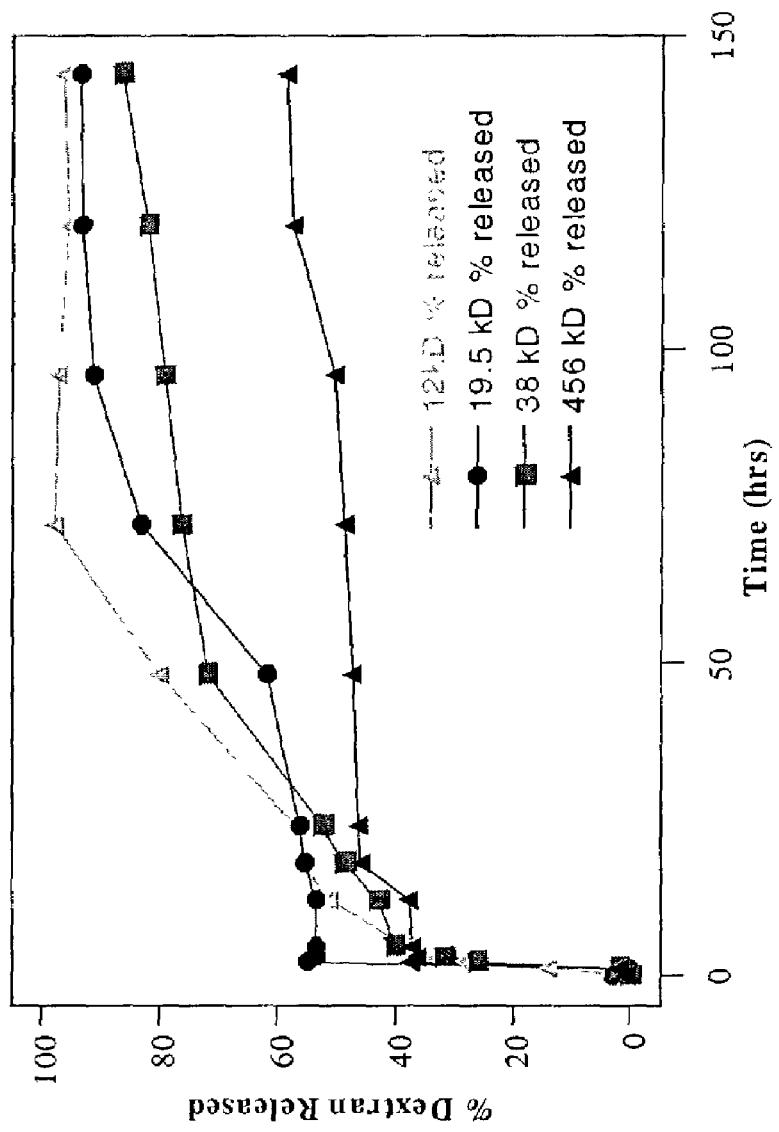
FIG. 12 is a plot of the release over time, in pH 7.4 PBS at 37° C., from an aggregate of polyHEMA hydrogel particles having a nominal diameter of 60 nanometers (nm), of various molecular weight FITC-labeled dextrans.

The minimum size of interstitial space between nanoparticles in an aggregate is 0.414 times the radius of the particles for a close packed array. This limits the size and diffusion rate of substances from an aggregate. Thus, using the loading technique described in Examples 10 and 11, FITC-labeled dextran molecules with average molecular weights of 12, 19.5, 38, and 456 kD were loaded into aggregates composed of 40 nm diameter polyHEMA nanoparticles. Dextran release was followed by UV visible spectroscopy. A plot showing the percent dextran released from an aggregate over time for different molecular weight dextran markers is shown in FIG. 12.

Example 13

Formation of Linear polyHEMA Microparticles

Seventy grams of extracted and distilled HEMA were combined with 65 grams of water containing 0.175 grams ammonium persulfate and 65 grams of water containing 0.175 grams sodium metabisulfite. The mixture was thoroughly mixed, transferred to a polyethylene heat sealable bag and $N_2$ was bubbled into the solution for twenty minutes. After sealing the bag, the solution was allowed to polymerize at room temperature undisturbed for twenty-four hours. The pliable, hydrated mass was cut into small pieces and leached in water for twenty-four hours under continuous stirring to remove unreacted monomers. The material was transferred to petri dishes and allowed to air dry in a hood. The resulting dry, brittle material was broken into small pieces in a Blender and then ground further in a lab grinder to reduce particle size further. The ground material was sieved to afford narrow ranges of different particle sizes. The size distribution was analyzed by optical microscopy and found to be in four groups: less than 50 micrometers, 50-150 micrometers, 150-250 micrometers, and greater than 250 micrometers. The particles swelled when placed in water, increasing in volume an average of 14 to 18%.

Example 14

Formation of Cross-Linked polyHEMA Microparticles

Seventy grams of extracted and distilled HEMA and 0.7 g ethyleneglycol dimethacrylate were combined with 65 grams of water containing 0.175 grams ammonium persulfate and 65 grams of water containing 0.175 grams sodium metabisulfite. The mixture was thoroughly mixed, transferred to a polyethylene heat sealable bag and $N_2$ was bubbled into the solution for twenty minutes. After sealing the bag, the solution was allowed to polymerize at room temperature undisturbed for twenty-four hours. The pliable, hydrated mass was cut into small pieces and leached in water for twenty-four hours under continuous stirring to remove unreacted monomers. The material was transferred to petri dishes and allowed to air dry in a hood. The dry, brittle material was broken into pieces in a Blender, and then ground in a lab grinder to reduce the particle size further. The ground material was sieved to afford narrow ranges of particle sizes. The size distributions were analyzed by optical microscopy and found to be in four groups: less than 50 micrometers, 50-150 micrometers, 150-250 micrometers, and greater than 250 micrometers. The particles swelled when placed in water, increasing in volume an average of 5 to 11%.

Example 15

Molding of Nano and Microparticle Aggregates

Unlike a bulk cross-linked polyHEMA hydrogel, it is possible to mold aggregates of polyHEMA micro and nanoparticles into various shapes. This has been demonstrated for nanoparticles produced from the aqueous polymerization described in Examples 1 and 2, and for microparticles produced in Examples 13 and 14. Thus, a suspension of hydrated nanoparticles was spun in a centrifuge tube at 100,000×G. The aggregate that formed was removed and placed between two polycarbonate blocks. Static pressure in excess of 500 kilograms/cm² was applied. The aggregates were left under this pressure for 30 minutes. The aggregates were compressed into thin films. Similar experiments with bulk cross-linked polyHEMA resulted in irreversible fragmentation. Hydrogel particles of polyHEMA with 0% to 30% co-monomer and diameters from 20 to 1000 nm were prepared and were found to be similarly moldable under applied pressure. Linear microparticles of the type in Example 13 were found to be moldable for sizes up to 150-250 micrometers (dry particle average size distribution). Particles above 250 micrometers fragmented. Cross-linked microparticles of the type in Example 14 were found to be moldable when the average size does not exceed 150 micrometers.

CONCLUSION

It will be appreciated that the hydrogel particle aggregates of this invention exhibit unique characteristics including, without limitation, shape-retentiveness, elasticity, controllable pore sizes and controllable degradation rates if desired that render them extremely useful for a wide variety of applications including, without limitation, the controlled release of biologically active substances, in vivo medical devices, tissue growth scaffolding and tissue replacement. Those skilled in the art will recognize that, while specific embodiments and examples have been described, various modifications and changes may be made without departing from the scope and spirit of this invention.

Other embodiments are contained within the claims that follow.

What is claimed:

1. A method for preparing a shape-retentive hydrogel aggregate composition comprising:
   (a) adding a monomer or two or more different monomers selected from the group consisting of a 2-alkenoic acid, a hydroxy(2C-4C)alkyl 2-alkenoate, a hydroxy(2C-4C) alkoxy(2C-4C)alkyl 2-alkenoate, a (IC-4C)alkoxy(2C-4C)alkoxy(2C-4C)alkyl 2-alkenoate and a vicinyl epoxy(1C-4C)alkyl 2-alkenoate to one or more liquid(s) having one or more hydroxyl groups;
   (b) adding from 0.1 to 15 mole percent of a cross-linking agent and from 0.01 to 10 mol percent of a surfactant to the liquid(s), where said surfactant is sodium dodecyl sulfaofate;
   (c) polymerizing the monomers to form a suspension in the liquid(s) of a plurality of hydrogel particles comprising a plurality of polymeric strands, wherein the hydrogel particles have an average diameter of less than 1,000 nanometers, and from 10 to 90% of absorbed liquids(s); and
   (d) removing non-absorbed liquids until the plurality of hydrogel particles coalesce into a shape-retentive aggregate held together by non-covalent inter-particle and particle-liquid physical forces, thereby forming a shape-retentive hydrogel aggregate composition.

2. A method for preparing a shape-retentive hydrogel aggregate composition, comprising:
   (a) adding a monomer or two or more different monomers selected from the group consisting of acrylic acid, methacrylic acid, 2-hydroxyethyl acrylate, 2-hydroxyethylmethacrylate, d iethyleneglycol monoacrylate, diethyleneglycol monomethacrylate, 2-hydroxypropyl acrylate, 2-hydroxypropyl methyacrylate, 3-hydroxypropylacrylate, 3-hydroxypropyl methacrylate, dipropylene glycol monoacrylate, dipropylene glycol monomethacrylate, 2,3-dihydroxypropyl methacrylate, glycidyl acrylate and glycidyl methacrylate, to one or more liquid(s) having one or more hydroxyl groups;
   (b) adding from 0.1 to 15 mole percent of a cross-linking agent and from 0.01 to 10 mol percent of a surfactant to the liquid(s), where said surfactant is sodium dodecyl sulfate;

(c) polymerizing the monomers to form a suspension in the liquid(s) of a plurality of hydrogel particles comprising a plurality of polymeric strands, wherein the plurality of hydrogel particles have an average diameter of less than 1,000 nanometers, and from 10 to 90% of absorbed liquids(s); and (d) removing non-absorbed liquid(s) until the hydrogel particles coalesce into a shape-retentive aggregate held together by non-covalent inter-particle and particle-liquid physical forces, thereby forming a shape-retentive hydrogel aggregate composition.

3. The method of claim 1, wherein the one or more monomers are selected from the group consisting of 2-hydroxyethyl methacrylate, methyacrylic acid, 2-aminoethyl-methacrylate, trimethylaminoethyl-methacrylate, glycerol methacrylate, 2-methoxyethyl methacrylate, glycidyl methacrylate, and hydroxypropyl methacrylate.

4. The method of claim 1 or 2, wherein the absorbed and non-absorbed liquids are independently selected from the group consisting of water, a (1C-10C) alcohol, a (2C-8C) polyol, a (1 C-4C)alkyl ether of a (2C-8C)polyol, a (10C-4C)acid ester of a (2C-8C)polyol; a hydroxy-terminated polyethylene oxide, a polyalkylene glycol and a hydroxy (2C-4C)alkyl ester of a mono, di- or tricarboxylic acid.

5. The method of claim 1 or 2, wherein the absorbed and the non-absorbed liquids are independently selected from the group consisting of water, methanol, ethanol, isopropyl alcohol, ethylene glycol, diethylene glycol, triethylene glycol, polyethylene glycol 200-600, propylene glycol, dipropylene glycol, 1,4-butanediol, 2,3-butanediol, 1,6-hexanediol, 2,5-hexanediol, ethylene glycol monomethyl ether, ethylene glycol monoethyl ether, methylcellosolve ether, ethylene glycol monoacetate, propylene glycol monomethyl ether, glycerine, glycerol monoacetate, tri(2-hyd roxyethyl) citrate, di(hyd roxypropyl)oxalate, glyceryl diacetate, and glyceryl monobutyrate.

6. The method of claim 1 or 2, wherein the absorbed liquid is water.

7. The method of claim 1 or 2, wherein the non-absorbed liquid is water.

8. The method of claim 1 or 2, wherein the absorbed and the non-absorbed liquid are water.

9. The method of claim 1 or 2, wherein the plurality of hydrogel particles is of narrow polydispersity.

10. The method of claim 1 or 2, wherein the one or more monomer(s) are uncharged, charged or a combination thereof.

11. The method of claim 1 or 2, wherein the plurality of hydrogel particles comprises particles of two or more different sizes and/or two or more different monomers.

12. The method of claim 1 or 2, wherein the cross-linking agent is an α-hydroxy acid ester.

13. The method of claim 1 or 2, wherein the cross-linking agent is selected from the group consisting of ethylene glycol diacrylate, ethylene glycol dimethylacrylate, 1,4-dihydrooxybutane dimethacrylate, dethylene glycol dimethyacrylate, propylene glycol dimethacrylate, diethylene glycol dimethacrylate, dipropylene glycol dimethacrylate, diethylene gycol diacrylate, dipropylene glycol diacrylate, divinyl benzene, divinyltoluene, diallyl tartrate, diallyl malate, divinyl tartrate, triallyl melamine, N,N'-methylene bisacryalamide, diallyl maleate, divinyl ether, 1,3-diallyl 2-(2-hydroxyethyl) citrate, vinyl allyl citrate, allyl vinyl maleate, diallyl itaconate, di(2-hydroxyethyl) itaconate, divinyl sulfone, hexahydro-1,3,5-triallyltriazine, triallyl phosphite, diallyl benzenephosphonate, triallyl aconitate, divinyl citraconate, trimethylolpropane trimethacrylate and diallyl fumarate.

14. The method of claim 1 or 2, further comprising adding a pharmaceutically active agent or a pharmaceutically acceptable excipient to the one or more liquid(s) liquid of step (a).

15. The method of claim 1 or 2, further comprising adding a pharmaceutically active agent or a pharmaceutically acceptable excipient to the polymerized polymer suspension formed in step (c).

16. The method of claim 1 or 2, wherein the at least one monomer is hydroxyethyl methacryate or hydroxypropyl methacrylate.

17. The method of claim 1 or 2, wherein the polymer consists essentially of a single monomer composition.

18. The method of claim 17, wherein the single monomer composition is selected from the group consisting of methacrylic acid, glycidyl methacrylate, hydroxyethyl methacrylate and hydroxypropyl methacrylate.

19. The method of claim 1 or 2, wherein the hydrogel particles of step (c) have an average diameter from 20 to 1000 nm.

* * * * *